United States Patent
Crabe et al.

(10) Patent No.: US 11,278,552 B2
(45) Date of Patent: Mar. 22, 2022

(54) COMBINATIONS INCLUDING ABX196 FOR THE TREATMENT OF CANCER

(71) Applicant: ABIVAX, Paris (FR)

(72) Inventors: Sandrine Crabe, Saint-Gély-du-Fesc (FR); Didier Scherrer, Castelnau le Lez (FR); Hartmut Ehrlich, Paris (FR); Philippe Pouletty, Paris (FR)

(73) Assignee: Abivax, Paris (FR)

( * ) Notice: Subject to any disclaimer, the term of this patent is extended or adjusted under 35 U.S.C. 154(b) by 0 days.

(21) Appl. No.: 16/333,531

(22) PCT Filed: Sep. 14, 2017

(86) PCT No.: PCT/EP2017/073202
§ 371 (c)(1),
(2) Date: Mar. 14, 2019

(87) PCT Pub. No.: WO2018/050782
PCT Pub. Date: Mar. 22, 2018

(65) Prior Publication Data
US 2019/0328747 A1     Oct. 31, 2019

(30) Foreign Application Priority Data
Sep. 14, 2016 (EP) .................................... 16306169

(51) Int. Cl.
| | |
|---|---|
| *A61K 31/553* | (2006.01) |
| *A61P 31/00* | (2006.01) |
| *A61P 35/00* | (2006.01) |
| *A61K 39/00* | (2006.01) |
| *A61K 39/39* | (2006.01) |
| *A61K 39/395* | (2006.01) |
| *C07K 16/28* | (2006.01) |
| *A61K 45/06* | (2006.01) |

(52) U.S. Cl.
CPC ........ *A61K 31/553* (2013.01); *A61K 39/0011* (2013.01); *A61K 39/001104* (2018.08); *A61K 39/001106* (2018.08); *A61K 39/001124* (2018.08); *A61K 39/001129* (2018.08); *A61K 39/001135* (2018.08); *A61K 39/001174* (2018.08); *A61K 39/39* (2013.01); *A61K 39/39558* (2013.01); *A61P 31/00* (2018.01); *A61P 35/00* (2018.01); *C07K 16/2818* (2013.01); *A61K 45/06* (2013.01); *A61K 2039/505* (2013.01); *A61K 2039/545* (2013.01); *A61K 2039/55516* (2013.01); *A61K 2039/55572* (2013.01)

(58) Field of Classification Search
None
See application file for complete search history.

(56) References Cited

U.S. PATENT DOCUMENTS

| | | | |
|---|---|---|---|
| 8,207,135 B2 | 6/2012 | Serra | |
| 8,685,408 B2 | 4/2014 | Tartour | |
| 8,835,613 B2* | 9/2014 | Berzofsky | ............... A61P 37/04 536/17.9 |
| 2009/0162385 A1 | 6/2009 | Serra | |
| 2013/0039886 A1 | 2/2013 | Berzofsky et al. | |

FOREIGN PATENT DOCUMENTS

| | | |
|---|---|---|
| CN | 101917985 A | 12/2010 |
| EP | 2172219 A1 | 4/2010 |
| JP | 2010083863 A | 4/2010 |
| JP | 2010514731 A | 5/2010 |
| JP | 2011506306 A | 3/2011 |
| WO | 2007/007946 A1 | 1/2007 |
| WO | 2007/118234 A2 | 10/2007 |
| WO | 2007118234 A3 | 10/2007 |
| WO | 2008/080926 A1 | 7/2008 |
| WO | 2009101475 A2 | 8/2009 |

OTHER PUBLICATIONS

Wilkinson, G. Pharmacokinetics, The Dynamics of Drug Absorption, Distribution, and Elimination (2001). In: Goodman and Gilman's the pharmacological basis of therapeutics. International edition, 10th edition, Mc Grow Hill, 971. (Year: 2001).*
Richly, H., Henning, B. F., Kupsch, P., Passarge, K., Grubert, M., Hilger, R. A., . . . & Flashar, C. (2006). Results of a Phase I trial of sorafenib (BAY 43-9006) in combination with doxorubicin in patients with refractory solid tumors. Annals of Oncology, 17(5), 866-873. (Year: 2006).*
International Search Report and Written Opinion from International Application No. PCT/EP2017/073202, dated Dec. 20, 2017.
European Search Report from corresponding European Application No. 16306169.0, dated Feb. 23, 2017.
Tefit, J. et al.: "Efficacy of ABX196, a new NKT agonist, in prophylactic human vaccination", Vaccine, Elsevier, Amsterdam, NL, vol. 32, No. 46, Sep. 13, 2014 (Sep. 13, 2014), pp. 6138-6145, XP029049158.
Oh, Hea Ry, et al., "Galactosylated Liposomes for Targeted Co-Delivery of Doxorubicin/Vimentin siRNA to Hepatocellular Carcinoma", Nanomaterials, 2016, 16 pages, vol. 6, No. 141.

* cited by examiner

*Primary Examiner* — Dale R Miller
(74) *Attorney, Agent, or Firm* — Merchant & Gould P.C.

(57) ABSTRACT

An antitumor pharmaceutical combination includes (i) a compound ABX196 and (ii) at least one chemotherapeutic agent and/or at least one immunotherapeutic agent, for use in the treatment of cancer.

10 Claims, 7 Drawing Sheets

Specification includes a Sequence Listing.

SEQUENCE LISTING

```
<160> NUMBER OF SEQ ID NOS: 4

<210> SEQ ID NO 1
<211> LENGTH: 31
<212> TYPE: PRT
<213> ORGANISM: Artificial Sequence
<220> FEATURE:
<223> OTHER INFORMATION: Amino acid sequence of peptide Cl II- TRP2(180-
      188)

<400> SEQUENCE: 1

Lys Phe Gly Trp Thr Gly Pro Asp Cys Asn Arg Lys Lys Pro Ala Gly
1               5                   10                  15

Gly Asn Cys Ser Val Tyr Asp Phe Phe Val Trp Leu His Tyr Tyr
            20                  25                  30

<210> SEQ ID NO 2
<211> LENGTH: 15
<212> TYPE: PRT
<213> ORGANISM: Artificial Sequence
<220> FEATURE:
<223> OTHER INFORMATION: Amino acid sequence of Class II epitope

<400> SEQUENCE: 2

Lys Phe Gly Trp Thr Gly Pro Asp Cys Asn Arg Lys Lys Pro Ala
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: Amino acid sequence of an immunodominant
      peptide from the tumor associated antigen tyrosinase-related
      protein-2

<400> SEQUENCE: 3

Ser Val Tyr Asp Phe Phe Val Trp Leu
1               5

<210> SEQ ID NO 4
<211> LENGTH: 32
```

```
<212> TYPE: PRT
<213> ORGANISM: Artificial Sequence
<220> FEATURE:
<223> OTHER INFORMATION: Amino acid sequence of a peptide comprising the
      sequence of an immunodominant peptide from TRP2

<400> SEQUENCE: 4

Gly Gly Gly Ser Val Tyr Asp Phe Phe Val Trp Leu Gly Gly Gly Ser
1               5                   10                  15

Ser Lys Phe Gly Trp Thr Gly Pro Asp Cys Asn Arg Lys Lys Pro Ala
            20                  25                  30
```

COMBINATIONS INCLUDING ABX196 FOR THE TREATMENT OF CANCER

This application is a National Stage Application of International Application No. PCT/EP2017/073202, filed 14 Sep. 2017, which claims benefit of Ser. No. 16/306,169.0, filed 14 Sep. 2016 in Europe and which applications are incorporated herein by reference. To the extent appropriate, a claim of priority is made to each of the above disclosed applications.

The present invention concerns new therapies for the treatment of cancers.

Cancer is a leading cause of mortality, despite years of research and treatment advances.

Numerous treatments exist, including chemotherapy and immunotherapy. However, even if these treatments may be effective i20ln some cases, they are generally very long and relapses are frequent. Additionally, they are responsible for numerous side effects which affect the patient's life quality.

New treatments act on aspects of cancerology which have been recently discovered, such as the implication of the immune system in the defense against cancer. However, these treatments are not always very effective.

There is thus an important need of improving the efficacy of current therapies, in particular chemotherapy and/or immunotherapy, preferably while reducing the side effects of these therapies.

The present invention arises from the unexpected finding by the inventors that the use of a specific NKT agonist, namely the α-galactosylceramide derivative ABX196 of formula (I)

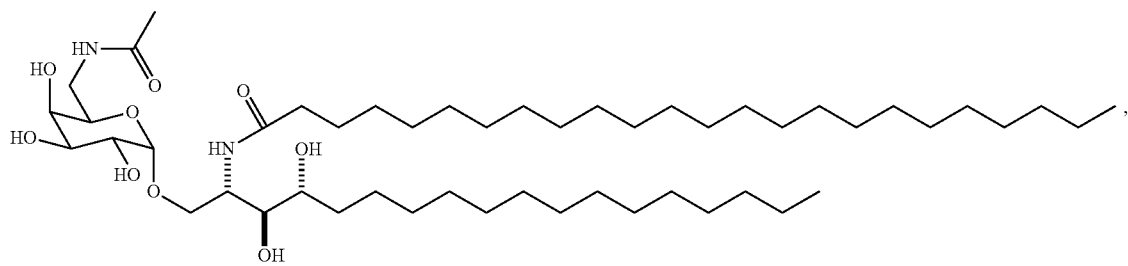

in combination with other known anticancerous treatments, in particular with chemotherapy and/or immunotherapy, enables significantly improving the efficacy of these known treatments, in particular against aggressive cancers.

In particular, the inventors discovered that the use of a vaccine composition comprising a compound ABX196 of formula (I)

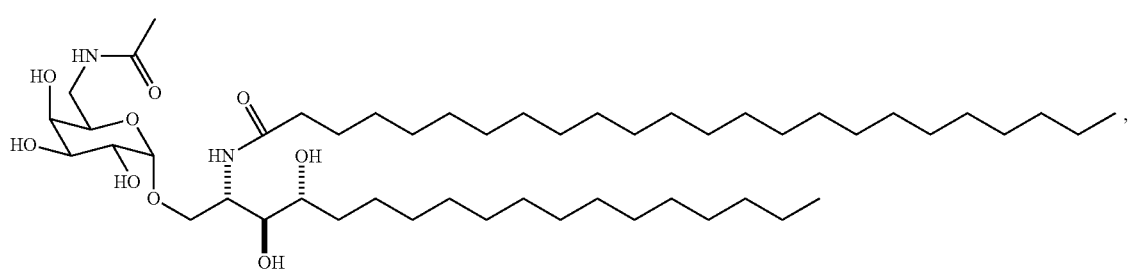

and a tumor antigen, in combination with other known anticancerous treatments, in particular with chemotherapy and/or immunotherapy, enables significantly improving the efficacy of these known treatments, in particular against aggressive cancers.

The inventors indeed demonstrated that the use of a vaccine composition comprising ABX196 and the tumor antigen Trp2, in combination with doxorubicin or anti-PD-1 monoclonal antibodies, improved the anti-tumor effects of these compounds in a melanoma mouse model.

The inventors also demonstrated that the use of ABX196 in combination with doxorubicin, sorafenib or anti-PD-1 monoclonal antibodies improved the anti-tumor effects of these compounds in a melanoma, colorectal cancer, bladder cancer and hepatocarcinoma mouse models, and further improved the survival of the mouse models.

The present invention thus concerns an antitumor pharmaceutical combination comprising:
(i) a compound ABX196 of formula (I)

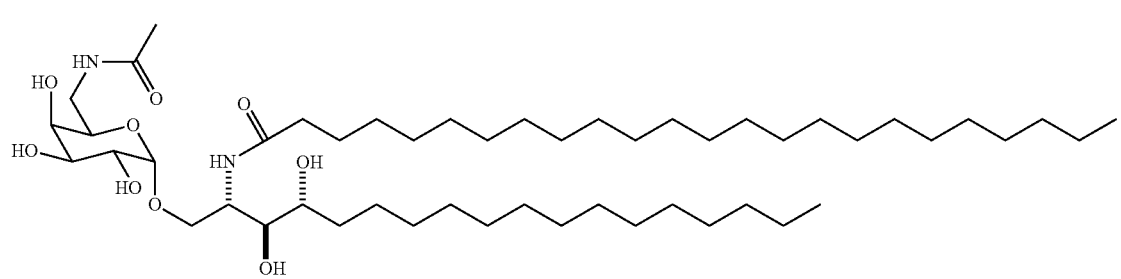

and,
(ii) at least one chemotherapeutic agent and/or at least one immunotherapeutic agent, for use in the treatment of cancer. In one embodiment, said antitumor pharmaceutical combination further comprises a tumor antigen. In a particular embodiment, the compound ABX196 of formula (I)

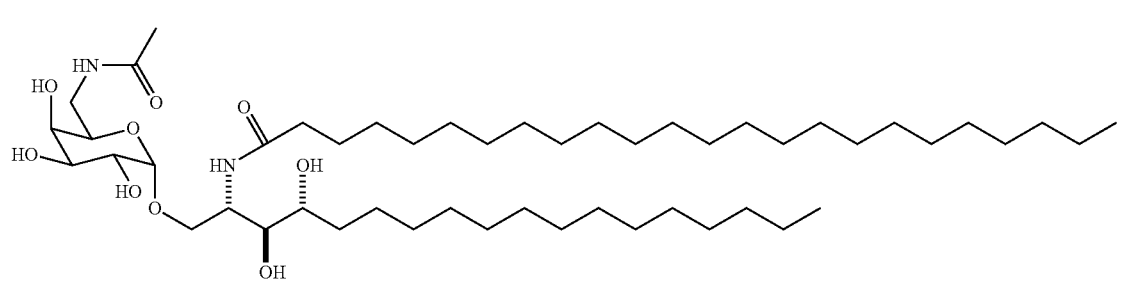

is comprised in a vaccine composition (iii) further comprising a tumor antigen.

Another object of the invention concerns a vaccine composition comprising a compound ABX196 of formula (I)

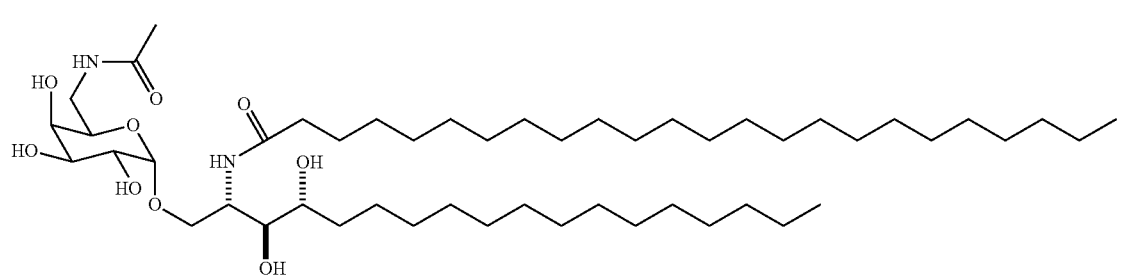

and a tumor antigen for use in combination with at least one chemotherapeutic agent and/or at least one immunotherapeutic agent in the treatment of a cancer.

The invention further concerns a compound ABX196 of formula (I)

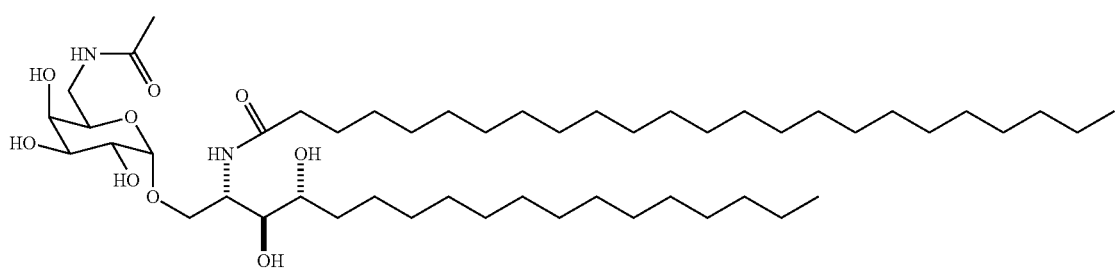

(I)

for use in combination with at least one chemotherapeutic agent and/or at least one immunotherapeutic agent in the treatment of cancer. In one embodiment, said combination further comprises a tumor antigen.

Another object of the invention concerns a combined preparation comprising:

(i) one or more dosage units of a compound ABX196 of formula (I)

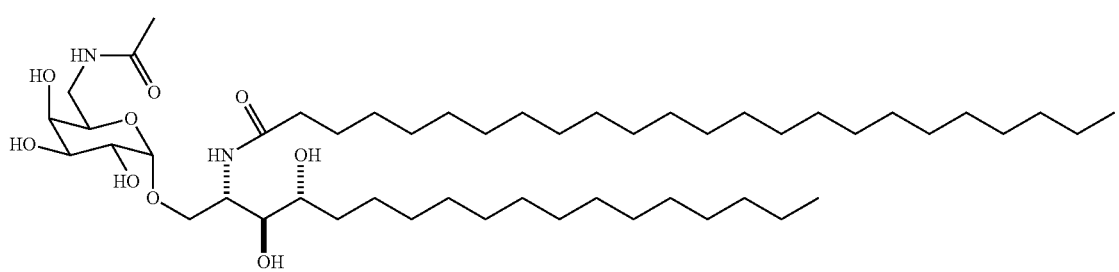

(I)

and (ii) one or more dosage units of at least one chemotherapeutic agent and/or one or more dosage units of an immunotherapeutic agent, for use in the treatment of cancer.

In one embodiment, in said combined preparation the compound ABX196 of formula (I)

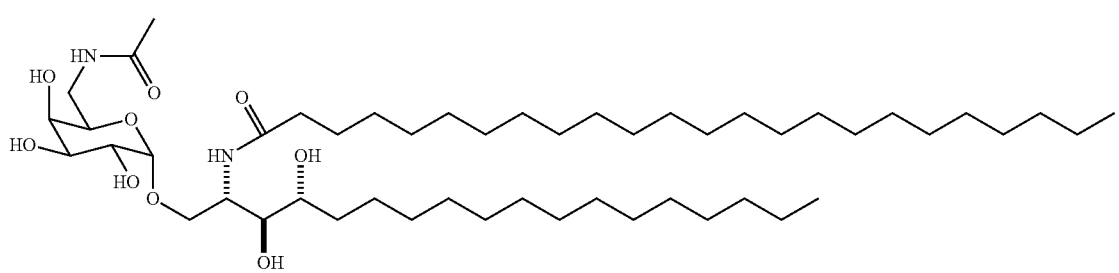

(I)

is comprised in a vaccine further comprising a tumor antigen.

In one embodiment, when the compound ABX196 as defined above is comprised in a vaccine composition according to the above objects of the invention, it is used as an adjuvant in said vaccine composition.

In particular, the percent treated/control (T/C (%)) index obtained for the combination of ABX196 with at least one chemotherapeutic agent and/or at least one immunotherapeutic agent is lower than the T/C (%) index obtained for the at least one chemotherapeutic agent alone and/or the at least one immunotherapeutic agent alone. In one embodiment, the T/C (%) of the combination of the invention is inferior or equal to 42%.

The percent treated/control (T/C (%)) index may be calculated by dividing the median treated tumor volume by the median control tumor volume and multiplying it by 100. For example, the median treated tumor volume is obtained following the administration of the combination of ABX196 with at least one chemotherapeutic agent and/or at least one immunotherapeutic agent according to the invention, and the median control tumor volume is obtained following the administration of the vehicle of said combination, said tumor volumes being assessed at the same time.

DETAILED DESCRIPTION OF THE INVENTION

Antitumor Pharmaceutical Combination

The compound ABX196, of formula (I)

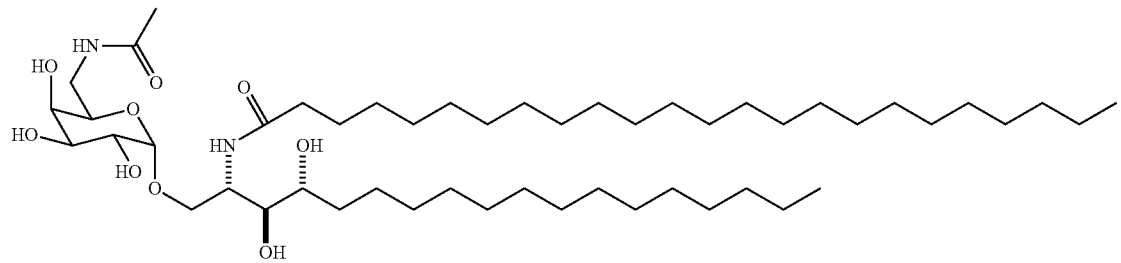

(I)

used according to the invention, is an α-galactosyl derivative which is known to stimulate NKT (Natural Killer T) cells. According to the present invention, the compound ABX196 also refers to its pharmaceutically acceptable salts. The term "pharmaceutically acceptable salt" refers to salts which retain the biological effectiveness and properties of ABX196 and which are not biologically or otherwise undesirable. For a review of pharmaceutically acceptable salts see Berge, et al. ((1977) J. Pharm. Sd, vol. 66, 1).

As used herein, the term "combination", "therapeutic combination" or "pharmaceutical combination", defines either a fixed combination in one dosage unit form or a kit of parts for the combined administration. In a particular embodiment, the compound ABX196 or the vaccine composition as defined below and the at least one chemotherapeutic agent and/or the at least one immunotherapeutic agent as defined below may be administered independently at the same time or separately within time intervals that allow that the combination partners show a synergistic effect.

In particular, when the compound ABX196 or the vaccine composition is used in combination with a chemotherapeutic agent, they may be administered independently at the same time or separately within time intervals. Similarly, when the compound ABX196 or the vaccine composition is used in combination with an immunotherapeutic agent, they may be administered independently at the same time or separately within time intervals.

Additionally, when the compound ABX196 or the vaccine composition is used in combination with more than one chemotherapeutic agent, each of the components of the combination may be administered independently at the same time or separately within time intervals, or some of the components of the combination may be administered independently at the same time while the other components of the combination may administered separately within intervals.

Similarly, when the compound ABX196 or the vaccine composition is used in combination with more than one immunotherapeutic agent, each of the components of the combination may be administered independently at the same time or separately within time intervals, or some of the components of the combination may be administered independently at the same time while the other components of the combination may administered separately within intervals.

Similarly, when the compound ABX196 or the vaccine composition is used in combination with a chemotherapeutic agent and an immunotherapeutic agent, each of the components of the combination may be administered independently at the same time or separately within time intervals, or some of the components of the combination may be administered independently at the same time while the other components of the combination may administered separately within intervals.

The constituents of which the combination is composed may be administered simultaneously, semi-simultaneously, separately, or spaced out over a period of time so as to obtain the maximum efficacy of the combination; it being possible for each administration to vary in its duration from a rapid administration to a continuous perfusion.

The compounds of the combination of the invention can thus be formulated in two, three or more separate pharmaceutical compositions.

The timing between at least one administration of the compound ABX196 or of the vaccine composition as defined in the section "Vaccine composition" above and at least one administration of the at least one chemotherapeutic agent as defined in the section "Chemotherapeutic agent" above is preferably about 4 days.

Preferably, the at least one chemotherapeutic agent as defined in the section "Chemotherapeutic agent" above is administered 4 days after the administration of the compound ABX196 or of the vaccine composition as defined in the section "Vaccine composition" above. Preferably, the at least one chemotherapeutic agent as defined in the section "Chemotherapeutic agent" above is administered 4 days before the administration of the compound ABX196 or of the vaccine composition as defined in the section "Vaccine composition" above.

The timing between at least one administration of the compound ABX196 or of the vaccine composition as defined in the section "Vaccine composition" above and at least one administration of the least one immunotherapeutic agent as defined in the section "Immunotherapeutic agent" above is preferably about 7 days.

Preferably, the at least one immunotherapeutic agent as defined in the section "Immunotherapeutic agent" above is administered 7 days after the administration of the compound ABX196 or of the vaccine composition as defined in the section "Vaccine composition" above. Preferably, the at least one immunotherapeutic agent as defined in the section "Immunotherapeutic agent" above is administered 7 days before the administration of the compound ABX196 or of the vaccine composition as defined in the section "Vaccine composition" above.

The compositions used in the context of the invention are preferably compositions which can be administered intravenously. However, these compositions may be administered orally, subcutaneously or intraperitoneally in the case of localized regional therapies. In one embodiment, these compositions are administered intratumorally.

The term "a combined preparation" is defined herein to refer to especially a "kit of parts" in the sense that the combination partners (i) and (ii), as defined above, can be dosed independently or by use of different fixed combinations with distinguished amounts of the combination partners, i.e., simultaneously or at different time points (this also applying for the different components of the partner (ii) when both a chemotherapeutic agent and an immunotherapeutic agent, or when several chemotherapeutic agents and/or several immunotherapeutic agents are used). The parts of the kit of parts can then e.g., be administered simultaneously or chronologically staggered, that is at different time points and with equal or different time intervals for any part of the kit of parts.

The combination partners of the combined preparation of the invention are preferably formulated in a dosage unit form. The term "dosage unit" refers to physically discrete units suitable as unitary dosages for human subjects and other mammals, each unit containing a predetermined quantity of active material(s) calculated to produce the desired therapeutic effect, optionally in association with a suitable pharmaceutical excipient.

The ratio of the total amounts of the combination partner (i) to the combination partner (ii) (or if applicable to the different components of the combination partner (ii)) to be administered in the combined preparation can be varied, e.g., in order to cope with the needs of a patient subpopulation to be treated or the needs of the single patient.

Vaccine Composition

The vaccine composition used in the context of the invention comprises the compound ABX196 of formula (I)

(DCC), DcR3, E6/E7, CGFR, EMBP, Dna78, farnesyl transferase, fibroblast growth factor-8a (FGF8a), fibroblast growth factor-8b (FGF8b), FLK-1/KDR, folic acid receptor, G250, G melanoma antigen gene family (GAGE-family), gastrin 17, gastrin-releasing hormone, ganglioside 2 (GD2)/ganglioside 3 (GD3)/ganglioside-monosialic acid-2 (GM2), gonadotropin releasing hormone (GnRH), UDP-GlcNAc: $R_1Man(\alpha1-6)R_2[GlcNAc$ to $Man(\alpha1-6)]\beta1,6$-N-acetylglucosaminyltransferase V (GnTV), GP1, gp100/Pmel-17, gp-100-in4, gp15, gp75/tyrosine-related protein-1 (gp75/TRP-1), human chorionic gonadotropin (hCG), heparanase, Her2/neu, EGFR, human mammary tumor virus (HMTV), 70 kD heat-shock protein (HSP70), human telomerase reverse transcriptase (hTERT), insulin-like growth factor receptor-1 (IGFR-1), interleukin-13 receptor (IL-13R), inducible nitric oxide synthase (iNOS), Ki67, KIAA0205, K-ras, H-ras, N-ras, KSA, LKLR-FUT, melanoma antigen-encoding family (MAGE-family, including at least MAGE-1, MAGE-2, MAGE-3, and MAGE-4), mammaglobin, MAP17, Melan-A/melanoma antigen recognized by T-cells-1 (MART-1), mesothelin, MIC A/B, MT-MMPs, mucin, testes-specific antigen NY-ESO-1, osteonectin, p15, P170/MDR1, p53, p97/melanotransferrin, PAI-1, platelet-derived growth factor (PDGF), PRAME, probasin, progenipoietin, prostate-specific antigen (PSA), prostate-specific membrane antigen (PSMA), prostatic acid phosphatase (PAP), RAGE-1, Rb, RCAS1, SART-1, SSX-family, STAT3, STn, TAG-72, transforming growth factor-α (TGF-α), transforming growth factor-β (TGF-β), uPA, uPAR, TNF-α Converting Enzyme (TACE), Thymosin-β-15, tumor necrosis factor-α (TNF-α), TP1, TRP-2, tyrosinase, vascular endothelial growth factor (VEGF), ZAG, p16INK4, PD-1, PD-L1, PD-L2, glypican-3, claudin-3, claudin-4, BMCA, and glutathione-S-transferase (GST).

Preferably, said tumor antigen is TRP-2.

In one embodiment, the sequence of said tumor antigen is selected from the group consisting of SEQ ID n° 1, SEQ ID n° 3 and SEQ ID n° 4, preferably SEQ ID n° 3.

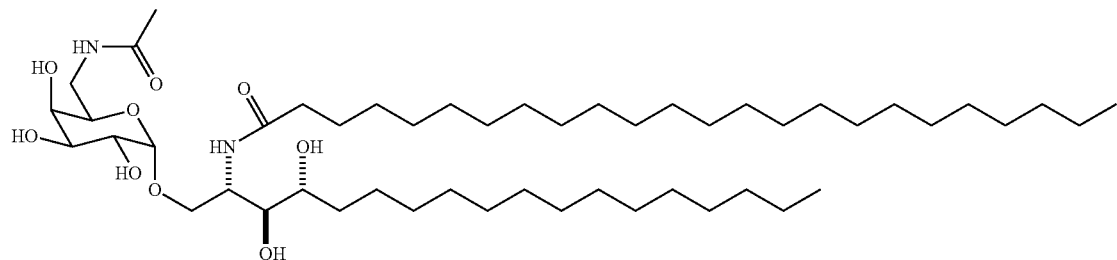

(I)

and a tumor antigen.

By "tumor antigen" is meant herein an antigen expressed exclusively on, associated with, or over-expressed in tumor tissue. Exemplary tumor antigens include, but are not limited to, 5-α-reductase, α-fetoprotein (AFP), AM-1, APC, APRIL, B melanoma antigen gene (BAGE), β-catenin, Bcl12, Bcr-Abl, Brachyury, CA-125, caspase-8 (CASP-8, also known as FLICE), Cathepsin S, CD19, CD20, CD21/complement receptor 2 (CR2), CD22/BL-CAM, CD23/FcεRII, CD33, CD35/complement receptor 1 (CRT), CD44/PGP-1, CD45/leucocyte common antigen (LCA), CD46/membrane cofactor protein (MCP), CD52/CAMPATH-1, CD55/decay accelerating factor (DAF), CD59/protectin, CDC27, CDK4, carcinoembryonic antigen (CEA), c-myc, cyclooxygenase-2 (cox-2), deleted in colorectal cancer gene Preferably, the tumor antigen is selected according to the specific cancer to be treated. The skilled person indeed knows which tumor antigen is specifically associated with a particular cancer. For example, it is well-known from the skilled person that the TRP-2 tumor antigen is expressed by melanoma cancer cells.

Accordingly, in a particularly preferred embodiment, the tumor antigen is TRP-2 and the cancer to be treated is melanoma.

The vaccine composition used in the context of the invention may comprise additional adjuvants. Additional adjuvants, other than ABX196, are well-known from the skilled person and include aluminium salts, oil-in-water emulsions such as Freund's incomplete adjuvant or MF59®, PRR ligands, TLR3 and RLR ligands such poly(I:C), TLR4 ligands such as LPS or monophosphoryl lipid A (MPLA), TLR5 ligands such as flagellin, TLR7/8 ligands such as imidazoquinolines, TLR9 ligands such as CpG oligodeoxynucleotides and NOD2 ligands such muramyl dipeptide (MDP).

However, since the compound ABX196 may be present as an adjuvant in the vaccine composition used in the context of the invention, in a preferred embodiment the vaccine composition only comprises the compound ABX196 as adjuvant. In a preferred embodiment, the compound ABX196 is used as an adjuvant is said vaccine composition according to the invention.

Chemotherapeutic Agents

As used herein, the term "chemotherapeutic agent" refers to any cell growth inhibitory compound or cytotoxic compound used in anticancerous chemotherapy. It is understood that such a compound is not an antigen. Such chemotherapeutic agents are well-known from the skilled person and include:
- alkylating agents, including nitrogen mustards such as cyclophosphamide, ifosfamide, mechlorethamine, chlorambucil and melphalan; ethyleneamines and methylmelamines such as thiotepa; methylhydrazine derivatives such as procarbazine; alkylsulfonates such as busulfan; nitrosoureas such as carmustine or lomustine; triazenes such as dacarbazine and temozolomide; platinum coordination complexes such as cisplatin, carboplatin and oxaliplatin;
- antimetabolites, including folic acid analogs such as methotrexate; pyrimidine analogs such as fluorouracil, cytarabine, gemcitabine and capecitabine; purine analogs such as mercaptopurine, pentostatin, cladribine and fludarabine;
- vinca alkaloids such as vinblastine, vinorelbine and vincristine;
- taxanes such as paclitaxel and docetaxel;
- epipodophyllotoxins such as etoposide and teniposide;
- camptothecins such as topotecan and irinotecan;
- anticancer antibiotics such as dactinomycin, daunorubicin, doxorubicin, plicomycin and epirubicin;
- anthracenediones such as mitoxantrone, mitomycin and bleomycin;
- mitotic inhibitors such as dolastatins;
- enzymes such as L-asparaginase;
- substituted ureas such as hydroxyurea;
- differentiating agents such as tretinoin;
- proteine kinase inhibitors such as imatinib or bryostatin;
- proteasome inhibitors such as geftinib and bortezomib;
- hormones and antagonists, including adrenocortical suppressants such as aminoglutethimide; adrenocorticosteroids such as prednisone; progestins such as megestrol acetate and medroxyprogesterone; estrogens such as diethylstilbestrol; anti-estrogens such as tamoxifen, idoxifen, droloxifene, zindoxifene, trioxifene, ICI 182, 780, EM-800 and toremifene; aromatase inhibitors such as anastrozole, letrozole and exemestane; androgens such as testosterone propionate; anti-androgens such as flutamide; and gonadotropin-releasing agents such as leuprolide.

Of course, any suitable combination of chemotherapeutic agents may be used, depending on the type of cancer.

In a preferred embodiment, the at least one chemotherapeutic agent is selected from the group consisting of doxorubicin, cyclophosphamide, epirubicin, idarubicin, mitoxantrone and oxaliplatin. In one embodiment, the at least one chemotherapeutic agent is doxorubicin or a kinase inhibitor such as sorafenib. Preferably, the at least one chemotherapeutic agent is doxorubicin or sorafenib, more preferably doxorubicin.

The at least one chemotherapeutic agent used in the context of the invention may be formulated in a pharmaceutical composition, which may further comprise pharmaceutically acceptable excipients, as defined below.

If a combination of different chemotherapeutic agents is used, these chemotherapeutic agents may be formulated in a single pharmaceutical composition or in separate pharmaceutical compositions.

The at least one chemotherapeutic agent used in the context of the invention may be administered by any suitable route well-known from the skilled person. As appreciated by skilled artisans, the pharmaceutical composition(s) comprising the chemotherapeutic agent(s) can be suitably formulated to be compatible with the intended route(s) of administration. Examples of suitable routes of administration include parenteral, e.g., intravenous, intradermal, subcutaneous, intramuscular, intraperitoneal, oral (e.g., buccal, inhalation, nasal and pulmonary spray), intradermal, transdermal (topical), transmucosal, intraocular and rectal administration.

Preferably, the at least one chemotherapeutic agent used in the context of the invention is administered intravenously.

The dosage regimen of the chemotherapeutic agent used in the context of the invention will depend on the specific agent used. Such dosage regimens are well-known from the skilled person. They typically combine a particular concentration of the administered chemotherapeutic agent and a particular administration scheme.

For example, doroxuribicin is preferably administered, by intravenous infusion of 3-5 min, at a dose of 40 to 75 mg/m$^2$ per cycle, each cycle being separated from the previous one by an interval of 3 to 4 weeks and the cycles being preferably repeated until achieving a maximal total dose of 550 mg/m$^2$.

However, since the combined use of the compound ABX196 or of the vaccine composition defined in the section "Vaccine composition" above with a chemotherapeutic agent increases significantly and synergically the anticancerous effects of said chemotherapeutic agent, it is possible to decrease the dose and/or the administration duration of the chemotherapeutic agent used compared to standard dosage regimens.

Accordingly, in a preferred embodiment, the at least one chemotherapeutic agent is administered at a dosage regimen lower than the standard dosage regimen recommended for this chemotherapeutic agent, in particular used alone or in combination with another chemotherapeutic agent and/or immunotherapeutic agent.

Immunotherapeutic Agents

As used herein, the term "immunotherapeutic agent" refers to an anticancerous agent, which mediates antineoplastic effects by initiating a novel or boosting an existing immune response against cancerous cells, such as antibodies or lymphocytes targeting a tumor antigen. The immunotherapeutic agent may be classified as "active" or "passive" based on its ability to (re-)activate the host immune system against malignant cells.

In one embodiment, said immunotherapeutic agent is not an antigen.

Preferably, the immunotherapeutic agent is an antibody specific of a tumor antigen, as defined in the section "Vaccine composition" above.

An "antibody" may be a natural or conventional antibody in which two heavy chains are linked to each other by disulfide bonds and each heavy chain is linked to a light chain by a disulfide bond. As used herein, the term "antibody" denotes conventional antibodies and fragments thereof, as well as single domain antibodies and fragments thereof, in particular variable heavy chain of single domain antibodies, and chimeric, humanized, bispecific or multispecific antibodies.

As used herein, antibodies also include "single domain antibodies" which are antibodies whose complementary determining regions are part of a single domain polypeptide. Examples of single domain antibodies include heavy chain antibodies, antibodies naturally devoid of light chains, single domain antibodies derived from conventional four-chain antibodies, engineered single domain antibodies. Single domain antibodies may be derived from any species including, but not limited to mouse, human, camel, llama, goat, rabbit and bovine. Single domain antibodies may be naturally occurring single domain antibodies known as heavy chain antibody devoid of light chains, such as those produced by *Camelidae* species, for example camel, dromedary, llama, alpaca and guanaco.

The variable heavy chain of these single domain antibodies devoid of light chains are known in the art as "VHH" or "nanobody". Similar to conventional VH domains, VHHs contain four FRs and three CDRs. Nanobodies have the advantage of being about ten times smaller than IgG molecules, and as a consequence properly folded functional nanobodies can be produced by in vitro expression while achieving high yield. Furthermore, nanobodies are very stable, and resistant to the action of proteases.

The term "monoclonal antibody" or "mAb" as used herein refers to an antibody molecule of a single amino acid composition that is directed against a specific antigen.

A monoclonal antibody may be produced by a single clone of B cells or hybridoma, but may also be recombinant, i.e. produced by protein engineering.

The term "chimeric antibody" refers to an engineered antibody which contains one or more region(s) from one antibody and one or more regions from one or more other antibody(ies). In particular a chimeric antibody comprises a VH domain and a VL domain of an antibody derived from a non-human animal, in association with a CH domain and a CL domain of another antibody, in particular a human antibody. As the non-human animal, any animal such as mouse, rat, hamster, rabbit or the like can be used. A chimeric antibody may also denote a multispecific antibody having specificity for at least two different antigens. In an embodiment, a chimeric antibody has variable domains of mouse origin and constant domains of human origin.

The term "humanized antibody" refers to an antibody which is initially wholly or partially of non-human origin and which has been modified to replace certain amino acids, in particular in the framework regions of the heavy and light chains, in order to avoid or minimize an immune response in humans. The constant domains of a humanized antibody are most of the time human CH and CL domains. In an embodiment, a humanized antibody has constant domains of human origin.

"Fragments" of (conventional) antibodies comprise a portion of an intact antibody, in particular the antigen binding region or variable region of the intact antibody. Examples of antibody fragments include Fv, Fab, F(ab')$_2$, Fab', dsFv, (dsFv)$_2$, scFv, sc(Fv)$_2$, diabodies, bispecific and multispecific antibodies formed from antibody fragments. A fragment of a conventional antibody may also be a single domain antibody, such as a heavy chain antibody or VHH.

The term "Fab" denotes an antibody fragment having a molecular weight of about 50,000 Da and antigen binding activity, in which about a half of the N-terminal side of H chain and the entire L chain, among fragments obtained by treating IgG with a protease, papaine, are bound together through a disulfide bond.

The term "F(ab')$_2$" refers to an antibody fragment having a molecular weight of about 100,000 Da and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 Da and antigen binding activity, which is obtained by cutting a disulfide bond of the hinge region of the F(ab')$_2$ fragment.

A single chain Fv ("scFv") polypeptide is a covalently linked VH::VL heterodimer which is usually expressed from a gene fusion including VH and VL encoding genes linked by a peptide-encoding linker. The human scFv fragment includes CDRs that are held in appropriate conformation, in particular by using gene recombination techniques. Divalent and multivalent antibody fragments can form either spontaneously by association of monovalent scFvs, or can be generated by coupling monovalent scFvs by a peptide linker, such as divalent sc(Fv)$_2$.

"dsFv" is a VH::VL heterodimer stabilised by a disulphide bond.

"(dsFv)$_2$" denotes two dsFv coupled by a peptide linker.

The term "bispecific antibody" or "BsAb" denotes an antibody which combines the antigen-binding sites of two antibodies within a single molecule. Thus, BsAbs are able to bind two different antigens simultaneously.

The term "multispecific antibody" denotes an antibody which combines the antigen-binding sites of two or more antibodies within a single molecule.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

In a particular embodiment, the immunotherapeutic agent used in the context of the invention is a monoclonal antibody or a fragment thereof, in particular a fragment selected from the group consisting of Fv, Fab, F(ab')$_2$, Fab', dsFv, (dsFv)$_2$, scFv, sc(Fv)$_2$, diabodies and VHH.

Most preferably, the immunotherapeutic agent used in the context of the invention is a monoclonal antibody.

Preferably, the immunotherapeutic agent used in the context of the invention is an antibody, in particular a monoclonal antibody, specific of a tumor antigen selected from the group consisting of Her2/neu, EGFR, VEGF, CD20, CD52, CD33, TACE, cathepsin S, uPA, uPAR, PD-1, Glypican-3, claudin-3, claudin-4, BMCA and CTLA4. In a particularly preferred embodiment, the immunotherapeutic agent used in the context of the invention is an antibody, in particular a monoclonal antibody, specific of PD-1. In one embodiment, the immunotherapeutic agent used in the context of the invention is an antibody selected from the group consisting of: anti-PD-1, anti-CTLA-4, anti-PD-L1, anti-GITR, anti-CD38, anti-4-1BB, anti-OX40, anti-LAG3 and anti-TIM-3.

In a particularly preferred embodiment, the immunotherapeutic agent is a monoclonal anti-PD1 antibody.

Examples of monoclonal antibodies specific of the above tumor antigens are well-known from the skilled person and include rituximab, trastuzumab (Herceptin), alemtuzumab, cetuximab, panitumumab, bevacizumab, ipilimumab, nivolumab (also known as MBS-936558, MDX-1106 or ONO-4538 anti-PD-1 antibody), pembrolizumab (also known as MK-3475 anti-PD-1 antibody), pidilizumab (also known as CT-011 anti-PD-1 antibody), BMS-936559 anti-PD-L1 antibody, MPDL3280A anti-PD-L1 antibody, MED14736 anti-PD-L1 antibody, MSB0010718C anti-PD-L1 antibody, D1(A12) anti-TACE antibody, A9 anti-TACE antibody, Fsn0503 h anti-cathepsin S antibody, ATN-658 anti-uPAR antibody, or the J6M0 anti-BMCA antibody.

Preferably, the immunotherapeutic agent used in the context of the invention is selected from the group consisting of nivolumab, pembrolizumab and pidilizumab.

The immunotherapeutic agent used in the context of the invention may also be a conjugate comprising a monoclonal antibody as defined above and a chemotherapeutic agent as defined in the section "Chemotherapeutic agent" above.

In another embodiment, the immunotherapeutic agent used in the context of the invention is an adoptively transferred T cell.

In the context of the invention, the term "adoptive cell transfer" refers to a variant of cell-based anticancer immunotherapy that generally involves (1) the collection of circulating or tumor-infiltrating lymphocytes, (2) their selection/modification/expansion/activation ex vivo and (3) their (re-)administration to patients, most often after lymphodepleting pre-conditioning and in combination with immunostimulatory agents.

The at least one immunotherapeutic agent used in the context of the invention may be formulated in a pharmaceutical composition, which may further comprise pharmaceutically acceptable excipients, as defined below.

If a combination of different immunotherapeutic agents is used, these immunotherapeutic agents may be formulated in a single pharmaceutical composition or in separate pharmaceutical compositions.

The at least one immunotherapeutic agent used in the context of the invention may be administered by any suitable route well-known from the skilled person. As appreciated by skilled artisans, the pharmaceutical composition(s) comprising the immunotherapeutic agent(s) can be suitably formulated to be compatible with the intended route(s) of administration. Examples of suitable routes of administration include parenteral, e.g., intravenous, intradermal, subcutaneous, intramuscular, intraperitoneal, oral (e.g., buccal, inhalation, nasal and pulmonary spray), intradermal, transdermal (topical), transmucosal, intraocular and rectal administration.

In one embodiment, the at least one immunotherapeutic agent used in the context of the invention is administered intravenously or intratumorally. Preferably, the at least one immunotherapeutic agent used in the context of the invention is administered intravenously.

The dosage regimen of the immunotherapeutic agent used in the context of the invention will depend on the specific agent used. Such dosage regimens are well-known from the skilled person. They typically combine a particular concentration of the administered immunotherapeutic agent and a particular administration scheme.

For example, nivolumab is preferably administered, by intravenous infusion of 60 min at a dose of 3 mg/kg of body weight every two weeks.

The immunotherapeutic agent used in the context of the invention is preferably administered over a cycle including multiple administrations, each administration being preferably separated of a time interval of 3 to 4 days.

However, since the combined use of the compound ABX196 or of the vaccine composition defined in the section "Vaccine composition" above with an immunotherapeutic agent increases significantly and synergically the anticancerous effects of said immunotherapeutically agent, it is possible to decrease the dose and/or the administration duration of the immunotherapeutic agent used compared to standard dosage regimens.

Accordingly, in a preferred embodiment, the at least one immunotherapeutic agent is administered at a dosage regimen lower than the standard dosage regimen recommended for this immunotherapeutic agent, in particular used alone or in combination with another immunotherapeutic agent and/or chemotherapeutic agent.

The pharmaceutical combination and/or the vaccine composition used in the context of the invention may further comprise pharmaceutically acceptable excipients.

"Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The pharmaceutical combination and/or the vaccine composition used in the context of the invention may be administered by any suitable route well-known from the skilled person. As appreciated by skilled artisans, the pharmaceutical combination and/or the vaccine composition can be suitably formulated to be compatible with the intended route of administration. Examples of suitable routes of administration include parenteral, e.g., intravenous, intradermal, subcutaneous, intramuscular, intraperitoneal, oral (e.g., buccal, inhalation, nasal and pulmonary spray), intradermal, transdermal (topical), transmucosal, intraocular and rectal administration.

Preferably, the pharmaceutical combination and/or the vaccine composition used in the context of the invention is administered intravenously, intramuscularly, subcutaneously, intranasally or intratumorally, more preferably intravenously. In one embodiment, the pharmaceutical combination and/or the vaccine composition used in the context of the invention is administered intravenously or intratumorally.

The pharmaceutical combination and/or the vaccine composition used in the context of the invention may be administered once to a patient in need thereof, or several times (including for example a prime dose followed by one or several booster dose(s)). Preferably, the vaccine composition used in the context of the invention is administered only once (and thus does not need any administration of any booster dose).

The pharmaceutical combination and/or the vaccine composition used in the context of the invention may be delivered in doses of compound ABX196 of at least 0.2 μg/patient. In one embodiment, the pharmaceutical combination and/or the vaccine composition used in the context of the invention may be delivered in doses of compound ABX196 of at least 3 ng/kg, for example between 3 ng/kg and 5 ng/kg. Effective doses will also vary depending on route of administration, as well as the possibility of co-usage with other agents.

Treatment of Cancer

The present invention further concerns a method of treating cancer, comprising the administration, in a patient in need thereof, of a therapeutically effective amount of an antitumor pharmaceutical combination, as defined in the section "Antitumor pharmaceutical combination" above, comprising:

(i) a compound ABX196 of formula (I)

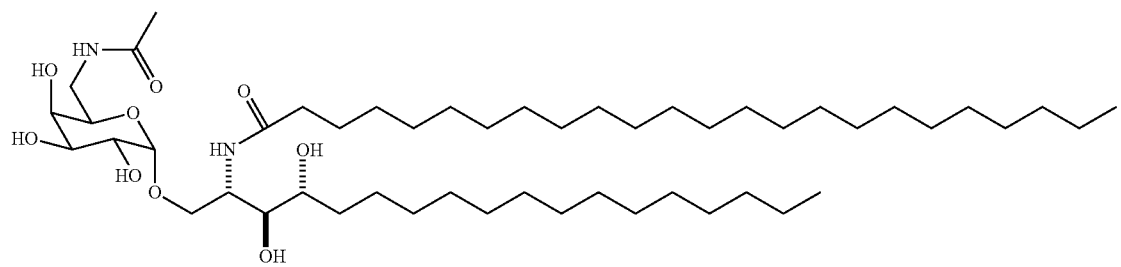

and, (ii) at least one chemotherapeutic agent, as defined in the section "Chemotherapeutic agent" above and/or at least one immunotherapeutic agent as defined in the section "Immunotherapeutic agent" above. In one embodiment, said ABX196 compound is comprised in a vaccine composition further comprising a tumor antigen, as defined in the section "Vaccine composition" above.

The present invention also concerns the use of:

(i) a compound ABX196 of formula (I)

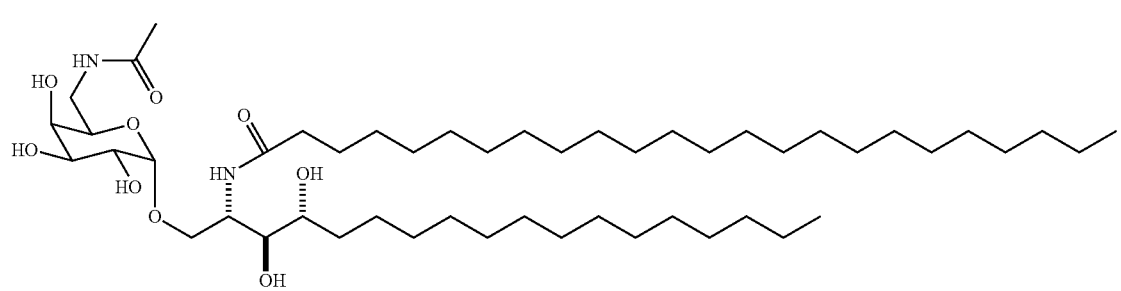

and, (ii) at least one chemotherapeutic agent, as defined in the section "Chemotherapeutic agent" above and/or at least one immunotherapeutic agent as defined in the section "Immunotherapeutic agent" above,
for the manufacture of an antitumor pharmaceutical combination intended for the treatment of cancer. In one embodiment, said ABX196 compound is comprised in a vaccine composition further comprising a tumor antigen, as defined in the section "Vaccine composition" above.

The present invention also concerns a method for treating cancer, comprising the administration, in particular the co-administration, in a patient in need thereof, of a therapeutically effective amount of a compound ABX196 of formula (I)

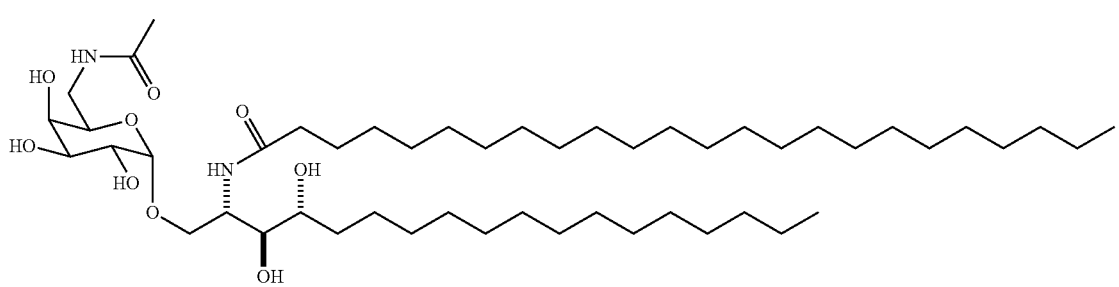

, in combination with a therapeutically effective amount of at least one chemotherapeutic agent, as defined in the section "Chemotherapeutic agent" above and/or a therapeutically effective amount of at least one immunotherapeutic agent as defined in the section "Immunotherapeutic agent" above. In one embodiment, said ABX196 compound is comprised in a vaccine composition further comprising a tumor antigen, as defined in the section "Vaccine composition" above.

The present invention also concerns the use of a compound ABX196 of formula (I)

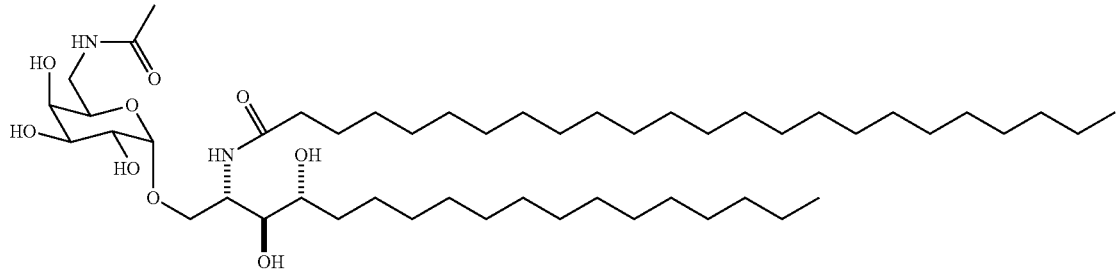

(I)

and a tumor antigen, as defined in the section "Vaccine composition" above, for the manufacture of a vaccine composition intended for the treatment of cancer in combination with at least one chemotherapeutic agent, as defined in the section "Chemotherapeutic agent" above and/or at least one immunotherapeutic agent as defined in the section "Immunotherapeutic agent" above.

The present invention also concerns a method for treating cancer, comprising the administration, in particular the co-administration, in a patient in need thereof, of a therapeutically effective amount of a compound ABX196 of formula (I)

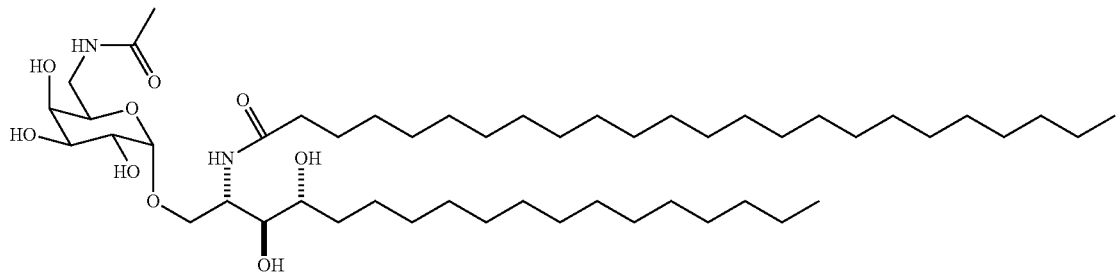

(I)

in combination with (a) a therapeutically effective amount of a tumor antigen, as defined in the section "Vaccine composition" above, and (b) a therapeutically effective amount of at least one chemotherapeutic agent, as defined in the section "Chemotherapeutic agent" above and/or a therapeutically effective amount of at least one immunotherapeutic agent as defined in the section "Immunotherapeutic agent" above.

The present invention also concerns the use of a compound ABX196 of formula (I)

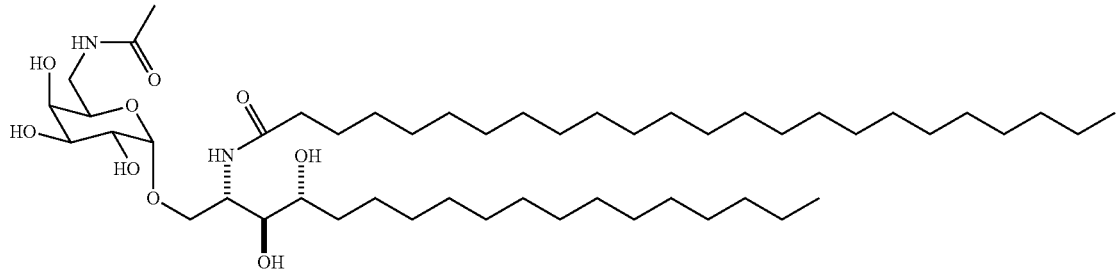

(I)

for the manufacture of a medicament intended for the treatment of cancer in combination with (a) a tumor antigen, as defined in the section "Vaccine composition" above, and (b) at least one chemotherapeutic agent, as defined in the section "Chemotherapeutic agent" above and/or at least one immunotherapeutic agent as defined in the section "Immunotherapeutic agent" above.

In all the above-mentioned aspects of the invention, the compound ABX196 when comprised in the vaccine composition, may be used as an adjuvant.

The term "co-administration" or "combined administration" as used herein is defined to encompass the administration of the selected therapeutic agents to a single patient, and are intended to include treatment regimens in which the agents are not necessarily administered by the same route of administration or at the same time.

According to the invention, the term "subject" or "subject in need thereof" is intended for a human or non-human mammal affected or likely to be affected with a cancer.

In the context of the invention, the term "treating" or "treatment" means reversing, alleviating, inhibiting the progress of, or preventing the disorder or condition to which such term applies, or one or more symptoms of such disorder or condition.

By a "therapeutically effective amount" of a compound of the invention is meant a sufficient amount of the compound to treat a cancer, (for example, to limit growth or to slow or block tumor metastasis) at a reasonable benefit/risk ratio applicable to any medical treatment. It will be understood, however, that the total daily usage of the compounds of the present invention will be decided by the attending physician within the scope of sound medical judgment. The specific therapeutically effective dose level for any particular subject will depend upon a variety of factors including the disorder being treating and the severity of the disorder, activity of the specific compounds employed, the specific combinations employed, the age, body weight, general health, sex and diet of the subject, the time of administration, route of administration and rate of excretion of the specific compounds employed, the duration of the treatment, drugs used in combination or coincidental with the specific compounds employed, and like factors well known in the medical arts. For example, it is well within the skill of the art to start doses of the compounds at levels lower than those required to achieve the desired therapeutic effect and to gradually increase the dosage until the desired effect is achieved.

The antitumor pharmaceutical combination according to the invention is particularly useful to treat cancers.

The antitumor pharmaceutical combination of the invention can be used to treat a perceptible cancerous tumor in any phase of its development, including a cancer in its advanced phase of evolution. In particular, the antitumor pharmaceutical combination of the invention can used to treat very aggressive cancers.

More particularly, the term "treatment of a cancer" as used herein includes at least one of the following features: alleviation of the symptoms associated with the cancer, a reduction in the extent of the cancerous tumor (e.g. a reduction in tumor growth), a stabilization of the state of the cancerous tumor (e.g. an inhibition of tumor growth), a prevention of further spread of the cancer (e.g. a metastasis), a prevention of the occurrence or recurrence of a cancer, a delaying or retardation of the progression of the cancer (e.g. a reduction in tumor growth) or an improvement in the state of the cancer (e.g. a reduction in tumor size).

As used herein the term "cancer" or "cancerous tumor" refers to a disorder in which a population of cells has become, in varying degrees, unresponsive to the control mechanisms that normally govern proliferation and differentiation. Cancer refers to various types of malignant neoplasms and tumors, including primary tumors, and tumor metastasis. Non-limiting examples of cancers which can be treated by the combinations of the present invention are lymphoproliferative disorders, breast cancer, ovarian cancer, prostate cancer, cervical cancer, endometrial cancer, bone cancer, liver cancer, stomach cancer, colon cancer, pancreatic cancer, cancer of the thyroid, head and neck cancer, cancer of the central nervous system, cancer of the peripheral nervous system, skin cancer, kidney cancer, hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, squamous cell carcinoma, basal cell carcinoma, adenocarcinoma, renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma, and hepatocarcinoma.

Preferably, the cancer to be treated in the context of the present invention is selected from the group consisting of melanoma, kidney cancer, hepatocarcinoma, pancreatic cancer and lung cancer.

In one embodiment, the cancer to be treated in the context of the present invention is selected from the group consisting of melanoma, hepatocarcinoma, bladder cancer and colorectal cancer.

Most preferably, the cancer to be treated in the context of the present invention is melanoma.

The combination therapy can provide a therapeutic advantage in view of the differential toxicity associated with the individual treatments. For example, treatment with one chemotherapeutic agent or with one immunotherapeutic agent can lead to a particular toxicity that is not seen with ABX196 or with the vaccine composition of the invention. As such, this differential toxicity can permit each treatment to be administered at a dose at which the toxicities do not exist or are minimal, such that together the combination therapy provides a therapeutic dose while avoiding the toxicities of each of the constituents of the combination agents. Furthermore, since the therapeutic effects achieved as a result of the combination treatment are enhanced, the doses of each of the agents can be reduced even further, thus lowering the associated toxicities to an even greater extent.

In a particularly preferred embodiment, the method of treatment of cancer according to the invention comprises one administration, preferably intravenously, of the compound ABX196 or of the vaccine composition of the invention, as defined in the section "Vaccine composition" above, followed, 4 days later, by one administration, preferably by intravenous infusion, of a chemotherapeutic agent, as defined in the section "Chemotherapeutic agent" above, in particular of doxorubicin.

In another embodiment, the method of treatment of cancer according to the invention comprises one administration, preferably intravenously, of the compound ABX196 or of the vaccine composition of the invention, as defined in the section "Vaccine composition" above, followed, 7 days later, by a first administration, preferably by intravenous infusion, of an immunotherapeutic agent as defined in the section "Immunotherapeutic agent" above, in particular of nivolumab, preferably followed, 4 days later, by a second administration, preferably by intravenous infusion, of said immunotherapeutic agent, preferably further followed, 3 days later, by a third administration, preferably by intravenous infusion, of said immunotherapeutic agent, further preferably followed, 4 days later, by a fourth administration, preferably by intravenous infusion, of said immunotherapeutic agent.

The present invention will be further illustrated by the figures and examples below.

*: $p<0.001$; **: $p<0.0001$; n.s.: not significant.

Figure 3:
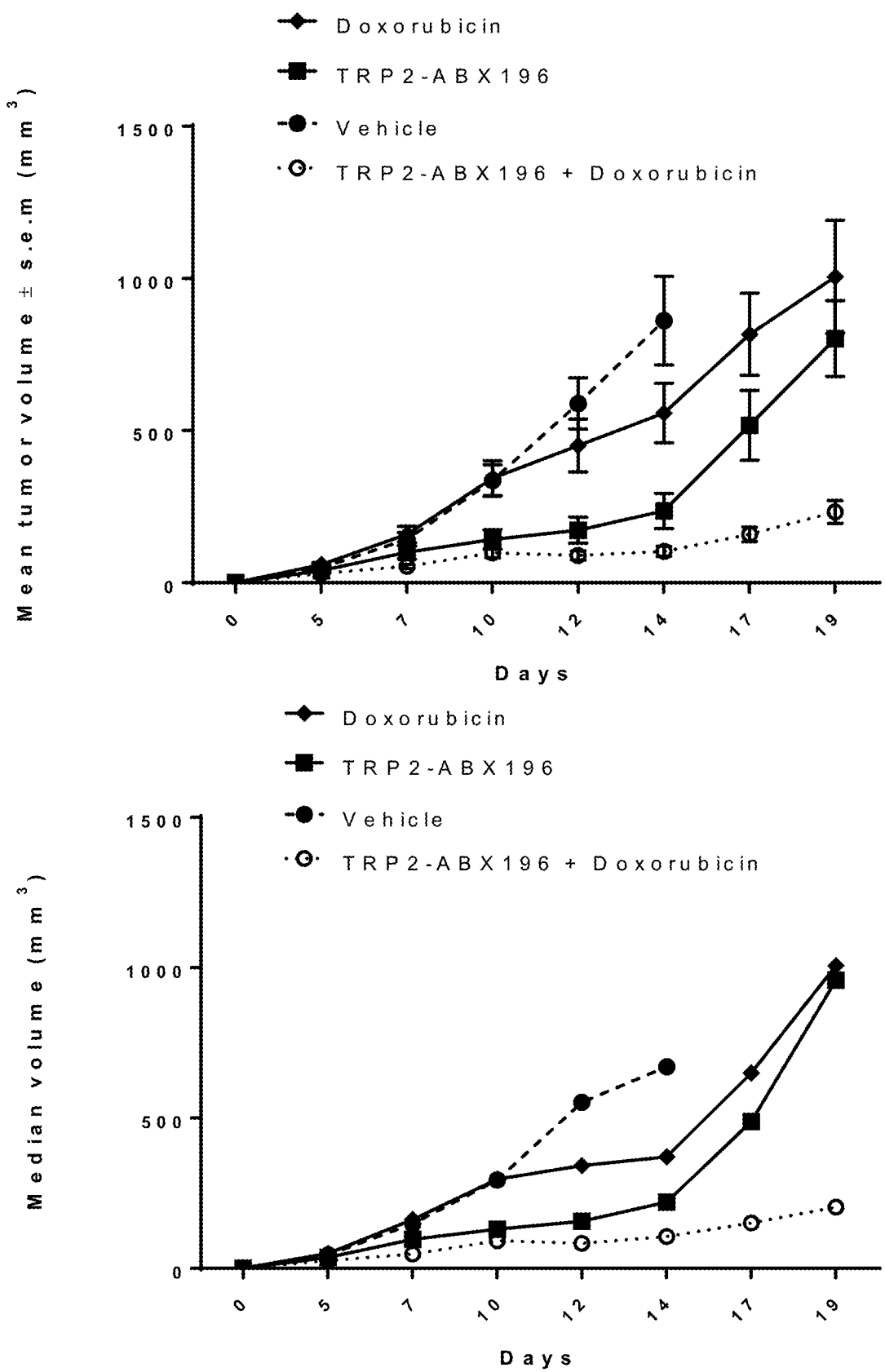

FIG. 3: Mean and median volume of B16-F10 tumors engrafted in C57BL/6 mice treated, in Example 1, with TRP2-ABX196 on D3, Doxorubicin on D7 or a combination of TRP2-ABX196 and Doxorubicin.

Figure 4:
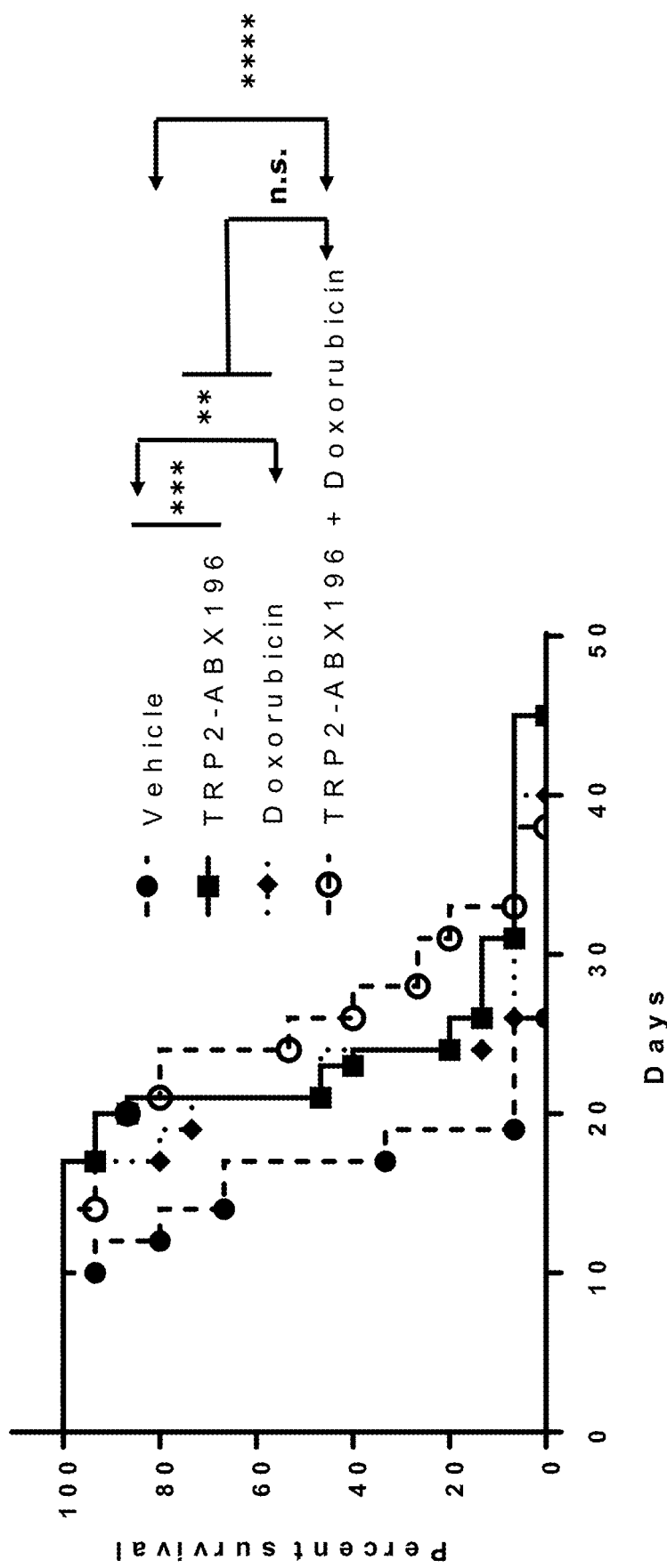

FIG. 4: Survival of C57BL/6 mice bearing B16-F10 tumors and treated, in Example 1, with TRP2-ABX196, Doxorubicin or a combination of TRP2-ABX196 and Doxorubicin. : $p<0.01$ *: $p<0.001$; ****: $p<0.0001$; n.s.: not significant.

Figure 5:
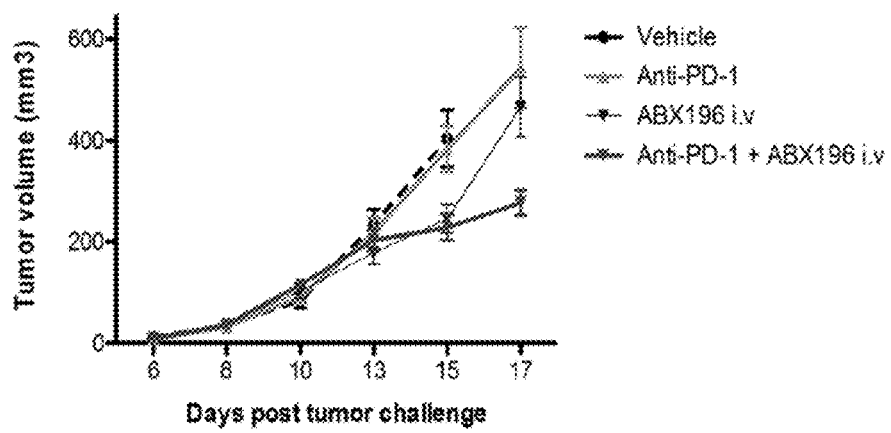

FIG. 5: Mean tumor volume (mm$^3$) of B16F10 bearing mice of example 5 exposed to vehicle, anti-PD-1 monoclonal antibodies, ABX196 administered i.v, or to the combination of anti-PD-1 monoclonal antibodies and ABX196 administered i.v. Mean+/−SEM.

Figure 6:
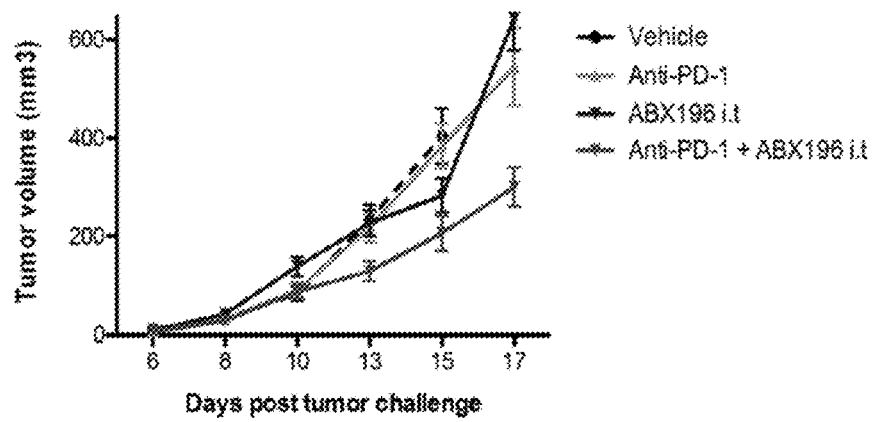

FIG. 6: Mean tumor volume (mm$^3$) of B16F10 bearing mice of Example 5 exposed to vehicle, anti-PD-1 monoclonal antibodies, ABX196 administered i.t, or to the combination of anti-PD-1 monoclonal antibodies and ABX196 administered i.t. Mean+/−SEM.

Figure 7:
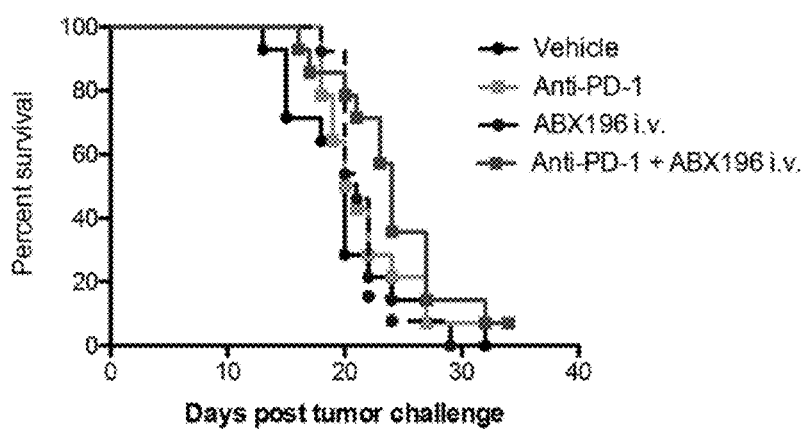

FIG. 7: Survival of B16F10 bearing mice of Example 5 exposed to vehicle, anti-PD-1 monoclonal antibodies, ABX196 administered i.v, or to the combination of anti-PD-1 monoclonal antibodies and ABX196 administered i.v. Mean+/−SEM.

Figure 8:
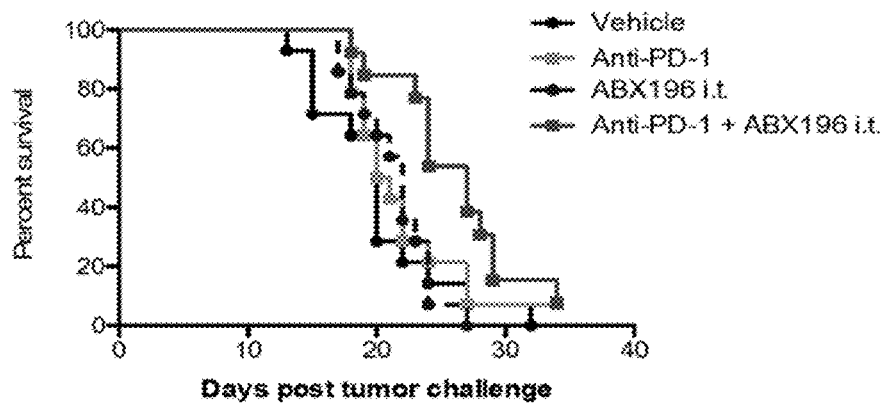

FIG. 8: Survival of B16F10 bearing mice of Example 5 exposed to vehicle, anti-PD-1 monoclonal antibodies, ABX196 administered i.t or to the combination of anti-PD-1 monoclonal antibodies and ABX196 administered i.t. Mean+/−SEM.

Figure 9:
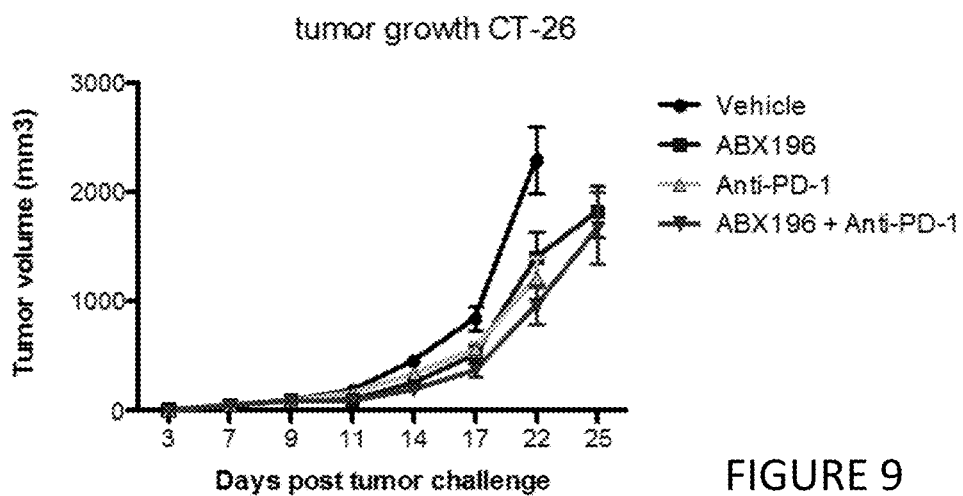

FIG. 9: Mean tumor volume (mm$^3$) of CT-26 bearing mice of Example 6 exposed to vehicle, anti-PD-1 monoclonal antibodies, ABX196 administered i.v, or to the combination of anti-PD-1 monoclonal antibodies and ABX196 administered i.v. Mean+/−SEM.

Figure 10:
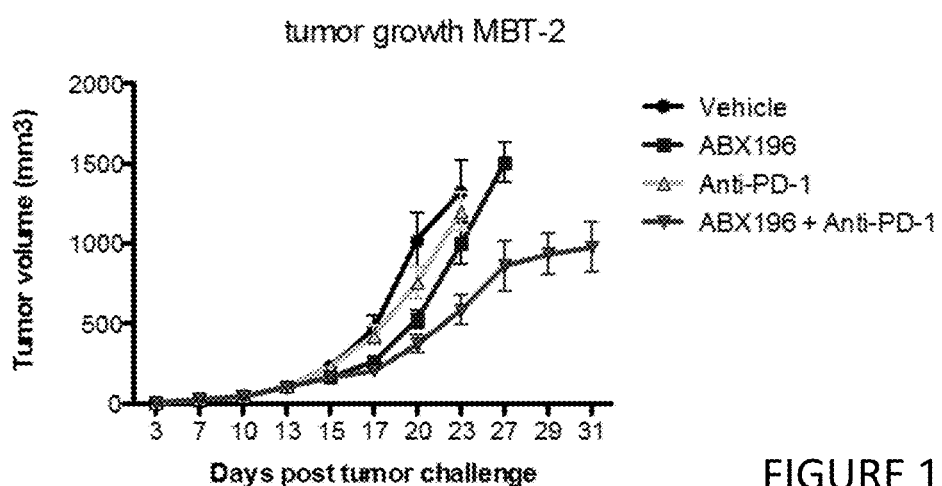

FIG. 10: Mean tumor volume (mm$^3$) of MBT-2 bearing mice of Example 6 exposed to vehicle, anti-PD-1 monoclonal antibodies, ABX196 administered i.v, or to the combination of anti-PD-1 monoclonal antibodies and ABX196. Mean+/−SEM FIG. 11: Survival of MBT-2 bearing mice of Example 6 exposed to vehicle (2), anti-PD-1 monoclonal antibodies (4), ABX196 administered i.v (3), or to the combination of anti-PD-1 monoclonal antibodies and ABX196 (1).

Figure 12:
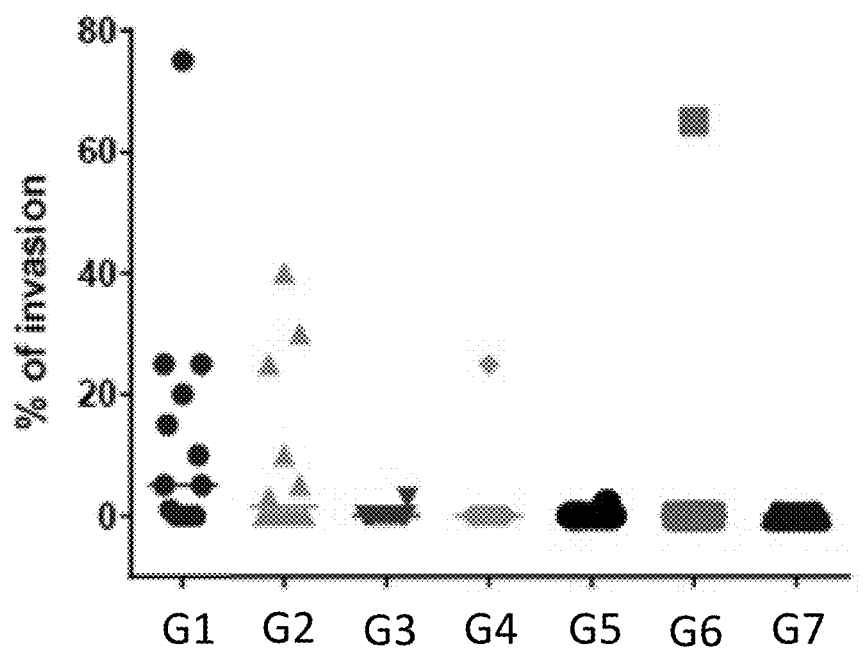

FIG. 12: % of tumor invasion of the liver from each groups of mice of Example 7 at day 20. G1: Vehicle; G2: Sorafenib; G3: Sorafenib+ABX196; G4: Doxorubicin; G5 Doxorubicin+ABX196; G6: Anti-PD-1; G7 Anti-PD-1+ ABX196

DESCRIPTION OF THE SEQUENCES

| SEQ ID NO: | Sequence | Description |
|---|---|---|
| 1 | KFGWTGPDCNRKKPA GGNCSVYDFFVWLHYY | Amino acid sequence of peptide CI II-TRP2$_{180-188}$ |
| 2 | KFGWTGPDCNRKKPA | Amino acid sequence of Class II epitope |
| 3 | SVYDFFVWL | Amino acid sequence of an immunodominant peptide from the tumor associated antigen tyrosinase-related protein-2 |
| 4 | GGGSVYDFFVWLGGGS SKFGWTGPDCNRKKPA | Amino acid sequence of a peptide comprising the sequence of an immunodominant peptide from TRP2 |

EXAMPLES

Example 1

This example demonstrates that a vaccine composition comprising the compound ABX196 and a tumor antigen increases the anticancerous effects of chemotherapeutic agents such as doxorubicin or immunotherapeutic agents such as anti-PD-1 antibodies.

1. Materials and Methods 1.1. Compounds

The vaccine composition used comprises the peptide CI II-TRP2$_{180-188}$ and the ABX196 adjuvant.

The peptide CI II-TRP2$_{180-188}$ of sequence KFGWTGPDCNRKKPA GG NCSVYDFFVWLHYY (SEQ ID NO: 1), is composed of a Class II epitope (KFGWTGPDCNRKKPA (SEQ ID NO: 2)) fused with an immunodominant peptide from the tumor associated antigen tyrosinase-related protein-2 which is over-expressed in melanocyte (SVYDFFVWL (SEQ ID NO: 3)).

The adjuvant ABX196 has the property to activate NKT cells.

The chemotherapeutic agent used was doxorubicin (DOXO CELL, Cell Pharm).

The immunotherapeutic agent used was anti-PD-1 antibody (ref.: BE0146, BioXcell; clone: RMP1-14, reactivity: mouse; isotype: Rat IgG2a; storage conditions: +4° C.).

1.2. Compounds Vehicles

Doxorubicin was diluted in NaCl 0.9%.

Anti-PD-1 antibody was prepared in phosphate buffered saline (PBS) or other suitable vehicle according to manufacturer's recommendation.

The CI II-TRP2 peptide (5 mg/tube) was resuspended in DMSO at a concentration of 50 mg/mL.

The adjuvant ABX196 was provided as a solution at 250 µg/mL

The final formulation of the vaccine containing CI II-TRP2 peptide and ABX196 were prepared in phosphate buffered saline (PBS).

The vehicle solution used in group 1 at day 3 (see section 2.1.2.) contained DMSO diluted in phosphate buffered saline (PBS) at the same final concentration as for the CL II-TRP2/ABX196 vaccine.

1.3. Treatment Doses

The peptide CI II-TRP2 was administered at the dose of 50 µg per mouse together with 1 µg of adjuvant ABX196.

The anti-PD-1 antibody was administered at the dose 10 mg/kg.

Doxorubicin was administered at the dose of 12 mg/kg.

1.4. Routes of Administration

The vaccine composition was injected by the intra-venous route in the caudal vein of mice (IV, bolus).

Anti-PD-1 antibody was injected into the peritoneal cavity of mice (Intraperitoneally, IP).

Doxorubicin was injected intravenously in the caudal vein of mice (IV, bolus).

In all groups, the vaccine composition was administered at a dose volume of 10 mL/kg/adm (i.e. for one mouse weighing 20 g, 200 µL of vaccine composition was administered) according to the most recent body weight of mice.

1.5. Cancer Cell Lines and Culture Conditions 1.5.1. Cancer Cell Lines

The cell line that was used is detailed in Table 1 below.

TABLE 1

| Cell lines used | | | |
|---|---|---|---|
| Cell line | Type | Specie | Origin |
| B16-F10 | Melanoma | mouse | ATCC[a] |

[a]American Type Culture Collection, Manassas, Virginia, USA The B16-F10 cell line was established from a lung metastasis arising from a spontaneously occurring melanoma in a C57BL/6J mouse.

1.5.2. Cell Culture Conditions

Cells were grown as monolayer at 37° C. in a humidified atmosphere (5% $CO_2$, 95% air) in their respective culture medium (see table below). The culture medium was DMEM containing 2 mM L-glutamine (ref: BE12-702F, Lonza, Verviers, Belgium) supplemented with 10% fetal bovine serum (ref: 3302, Lonza). Tumor cells are adherent to plastic flasks. For experimental use, tumor cells were detached from the culture flask by a 5-minute treatment with trypsin-versene (ref: BE17-161E, Lonza), in Hanks' medium without calcium or magnesium (ref: BE10-543F, Lonza) and neutralized by addition of complete culture medium. The cells were counted in a hemocytometer and their viability was assessed by 0.25% trypan blue exclusion assay.

1.6. Use of Animals 1.6.1. Animals 95 healthy female C57BL/6 (C57BL/6J) mice, 6-7 weeks old, were obtained from JANVIER LABS (Le Genest-Saint-Isle, France). Animals were maintained in SPF health status according to the FELASA guidelines.

Animal housing and experimental procedures were realized according to the French and European Regulations and NRC Guide for the Care and Use of Laboratory Animals.

1.6.2. Housing Conditions

Animals were maintained in housing rooms under controlled environmental conditions:

Temperature: $22\pm2°$ C.,

Humidity $55\pm10\%$,

Photoperiod (12 h light/12 h dark),

HEPA filtered air, 15 air exchanges per hour with no recirculation.

Animal enclosures were provided sterile and adequate space with bedding material, food and water, environmental and social enrichment (group housing) as described:

Top filter polycarbonate Eurostandard Type III or IV cages,

Corn cob bedding (ref: LAB COB 12, SERLAB, France), 25 kGy Irradiated diet (Ssniff® Soest, Germany), Complete food for immunocompetent rodents—R/M-H Extrudate, Sterile, filtrated at 0.2 µm water, Environmental enrichment (SIZZLE-dri kraft—D20004 SERLAB, France).

2. Treatments 2.1. Antitumor Activity Study of a Novel Vaccine in Combination with PD-1 Targeting Antibody or Doxorubicin in Mice Bearing Subcutaneous 816-F10 Melanoma 2.1.1. Induction of B16-F10 Tumors in Animals Tumor was induced by subcutaneous injection of $1\times10^6$ of B16-F10 cells in 200 µL of PBS buffer into the right flank of 95 C57BL/6 female animals. The day of tumor cell injection in the right flank was considered as D0.

2.1.2. Treatment Schedule

On D3, 90 out of ninety-five 95 were then randomized according to their body weight into 6 groups each of 15 animals (groups 1-6).

A statistical test (analysis of variance, ANOVA) was performed to test for homogeneity between groups using the Vivo Manager® software (Biosystemes, Couternon, France).

Animals from group 1 received one IV injection of the vehicle used for the vaccine composition at day 3 and 4 IP administrations of the vehicle used for anti-PD-1 antibody on day 10, 14, 17 and 21.

Animals from group 2 received one IV injection of 50 µg of CI II-TRP2 together with 1 µg of ABX196 on day 3.

Animals from group 3 received 4 IP administrations of anti-PD-1 antibody on day 10, 14, 17 and 21.

Animals from group 4 received one IV injection of 50 µg of CL II-TRP2 together with 1 µg of ABX196 at day 3 and 4 IP administrations of anti-PD-1 antibody on day 10, 14, 17 and 21.

Animals from group 5 received one IV injection of Doxorubicin at 12 mg/kg on day 7.

Animals from group 6 received one IV injection of 50 µg of CL II-TRP2 together with 1 µg of ABX196 on day 3 and one IV injection of Doxorubicin at 12 mg/kg on day 7.

The treatment schedule is summarized in Table 2 below.

TABLE 2

Treatment schedules

| Group | No. Animals | Treatment | Dose | Route | Treatment Schedule |
|---|---|---|---|---|---|
| 1 | 15 | Vehicle | — | IV/IP | D3-IV/TWx2 IP |
| 2 | 15 | CL II-TRP2/ABX196 | 50 µg/1 µg | IV | Q1Dx1 on D3 |
| 3 | 15 | Anti-PD-1 Ab | 10 mg/kg | IP | TWx2 on D10/D14/D17/D21 |
| 4 | 15 | CL II-TRP2/ABX196 | 50 µg/1 µg | IV | Q1Dx1 on D3 |
|   |   | Anti-PD-1 Ab | 10 mg/kg | IP | TWx2 on D10/D14/D17/D21 |
| 5 | 15 | Doxorubicin | 12 mg/kg | IV | Q1Dx1 on D7 |
| 6 | 15 | CL II-TRP2/ABX196 | 50 µg/1 µg | IV | Q1Dx1 on D3 |
|   |   | Doxorubicin | 12 mg/kg | IV | Q1Dx1 on D7 |
| TOTAL | 90 |   |   |   |   |

The monitoring of animals was performed as described in section 2.2.

2.2. Animal Monitoring 2.2.1. Clinical Monitoring

The viability and behavior were recorded every day. Body weights were measured twice a week until injection of tumor cells then thrice a week. The length and width of the tumor were measured thrice a week with calipers and the volume of the tumor was estimated by the formula:

$$\text{Tumor volume} = \frac{\text{width}^2 \times \text{length}}{2}$$

2.2.2. Humane Endpoints

Signs of pain, suffering or distress: pain posture, pain face mask, behavior,

Tumor exceeding 10% of normal body weight (individual tumor taken into account), but non-exceeding 1,500 mm$^3$ (the sum of tumor volume on right flank/MFP and tumor volume on left flank/MFP were taken into account), Tumors interfering with ambulation or nutrition, Ulcerated tumor or tissue erosion, 20% body weight loss remaining for 2 consecutive days, Poor body condition, emaciation, cachexia, dehydration, Prolonged absence of voluntary responses to external stimuli, Rapid labored breathing, anemia, significant bleeding, Neurologic signs: circling, convulsion, paralysis, Sustained decrease in body temperature, Abdominal distension.

2.2.3. Necropsy

Necropsy (macroscopic examination) was performed on all terminated animals in the study, and, if possible, on all euthanized moribund or found dead animals.

2.3. Animal Procedures 2.3.1. Anesthesia

Isoflurane gas anesthesia was used for tumor inoculation and i.v. injections.

2.3.2. Euthanasia

Euthanasia of animals was performed by gas anesthesia over-dosage (Isoflurane) followed by cervical dislocation or exsanguination.

3. Data Processing 3.1. Health Parameters

The following evaluation criteria of health were determined using Vivo Manager® software (Biosystemes, Couternon, France):

Individual and mean body weights of animals were provided.

Mean body weight change (MBWC): Average weight changes of treated animals in percent (weight at day B minus weight at day A divided by weight at day A) were calculated. The intervals over which MBWC was calculated, was chosen as a function of body weight curves and the days of body weight measurement.

3.2. Efficacy Parameters

The treatment efficacy was assessed in terms of the effects of the vaccine composition on the tumor volumes of treated animals relative to control animals. The following evaluation criteria of antitumor efficacy was determined using Vivo Manager® software (Biosystemes, Couternon, France):

Individual, mean and median tumor volumes were provided,

The number of tumor-free mice was provided.

Mice survival was also monitored and used as an efficacy parameter. Survival curves were drawn.

Percent treated/control (T/C (%) index) is calculated by dividing the median treated tumor volume by the median control tumor volume on day 14 and multiplying by 100. A T/C % equal or less than 42% is considered significant antitumor activity by the drug evaluation branch of the division of cancer treatment (NCI).

$$T/C\ \% = \frac{\text{Tumor Volume Median}_{treated}}{\text{Tumor Volume Median}_{vehicle}} \times 100$$

Tumor growth inhibition is also reflective to the antitumor effectiveness and is calculated following the formula:

$$TGI\ \% = \left[ \frac{1 - \left(\frac{TVM_{treated\ dayx}}{TVM_{treated\ initial}}\right)}{1 - \left(\frac{TVM_{vehicle\ initial}}{TVM_{vehicle\ dayx}}\right)} \left(\frac{TVM_{vehicle\ dayx}}{TVM_{vehicle\ initial}}\right) \right] \times 100$$

% TGI higher than 50% is considered as active.

3.3. Statistical Analysis

Mean tumor volumes at defined times were analyzed with the GrapadPrism Software (Version 6.07) using the Kruskall-Wallis test for all the treatments. A significant difference between all treatments (P<0.05) was followed by pairwise comparisons using the Dunn's multiple comparison test. Survival was analyzed using the Log-rank (Mantel-Cox) test with GrapadPrism Software (Version 6.07). A significant difference between all treatments (P<0.05) was followed by pairwise comparisons using the Log-rank (Mantel-Cox) test.

4. Results 4.1. Antitumor Activity Study of the Vaccine Composition of the Invention (TRP2-ABX196) in Combination with PD-1 Targeting Antibody or Doxorubicin in Mice Bearing Subcutaneous B16-F10 Melanoma 4.1.1. Toxicity Parameters The mean body weight curves were determined, and the effects of treatments on mice individual body weight were studied.

No deterioration in general status was observed and clinical status remained good for treated animals during the study whatever the treatment group.

For the three groups of mice that were immunized with TRP2-ABX196, an important weight loss, i.e. approximately 10%, was measured two days after immunization. The weight loss was transient in all the mice and they rapidly recovered weight at day five.

With the exception of mice treated with a combination of TRP2-ABX196 and doxorubicin, in which body weight was stabilized during the treatment period, the weight evolution was similar in all the other treatment groups.

Thus, with the exception of a transient weight loss after administration of the vaccine TRP2-ABX196 alone or in combination, all treatments were well tolerated by C57BL/6J mice bearing B16-F10 tumor.

4.1.2. Antitumor Activity Analysis

Figure 1:
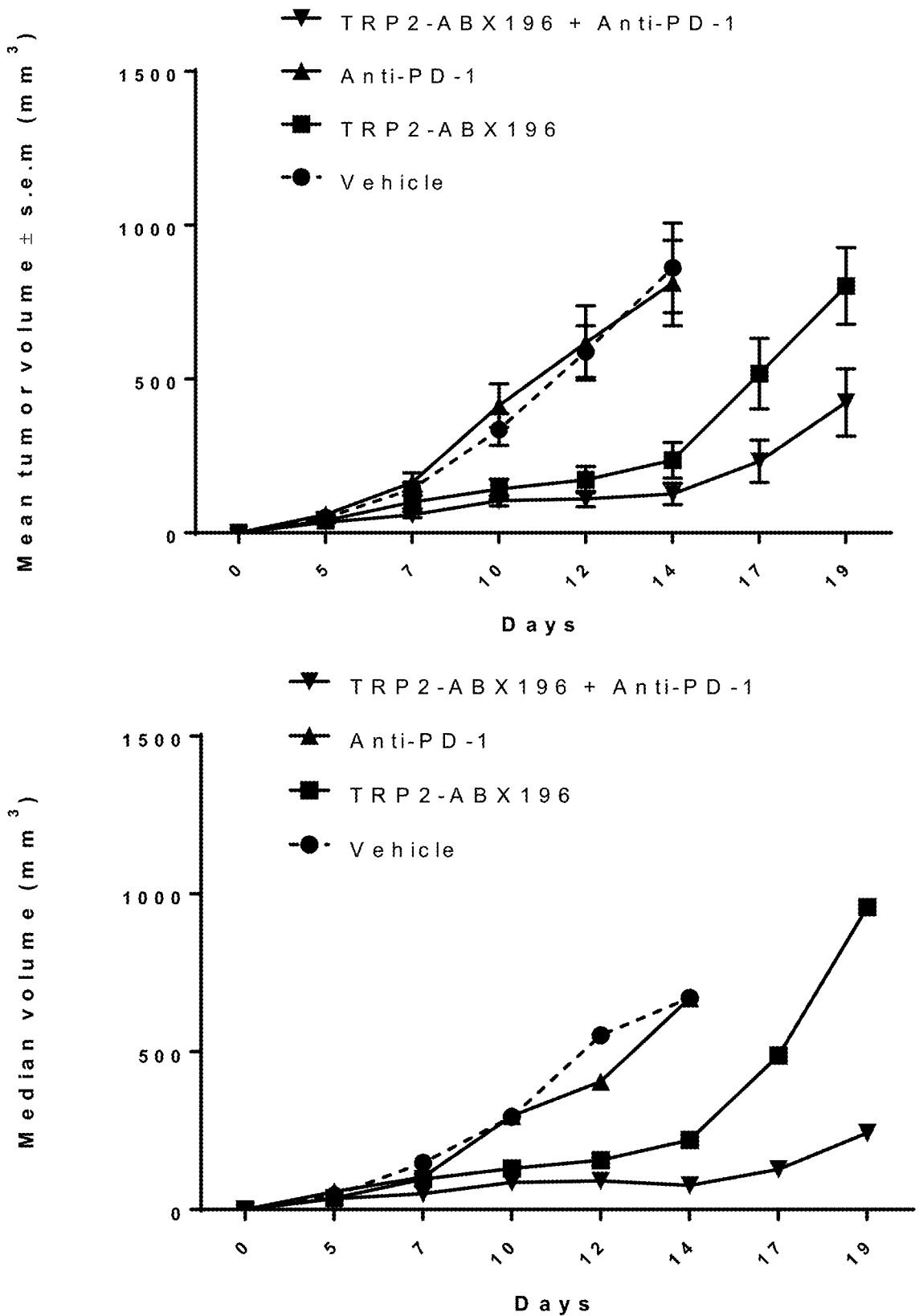
FIG. 1: Mean and median volume of B16-F10 tumors engrafted in C57BL/6 mice treated, in Example 1, with TRP2-ABX196 on D3, anti-PD-1 antibodies on D10, D14, D17 and D21 or a combination of TRP2-ABX196 and anti-PD-1 antibodies.

The individual, mean and median tumor volumes curves are presented in FIGS. 1 and 3.

Figure 2:
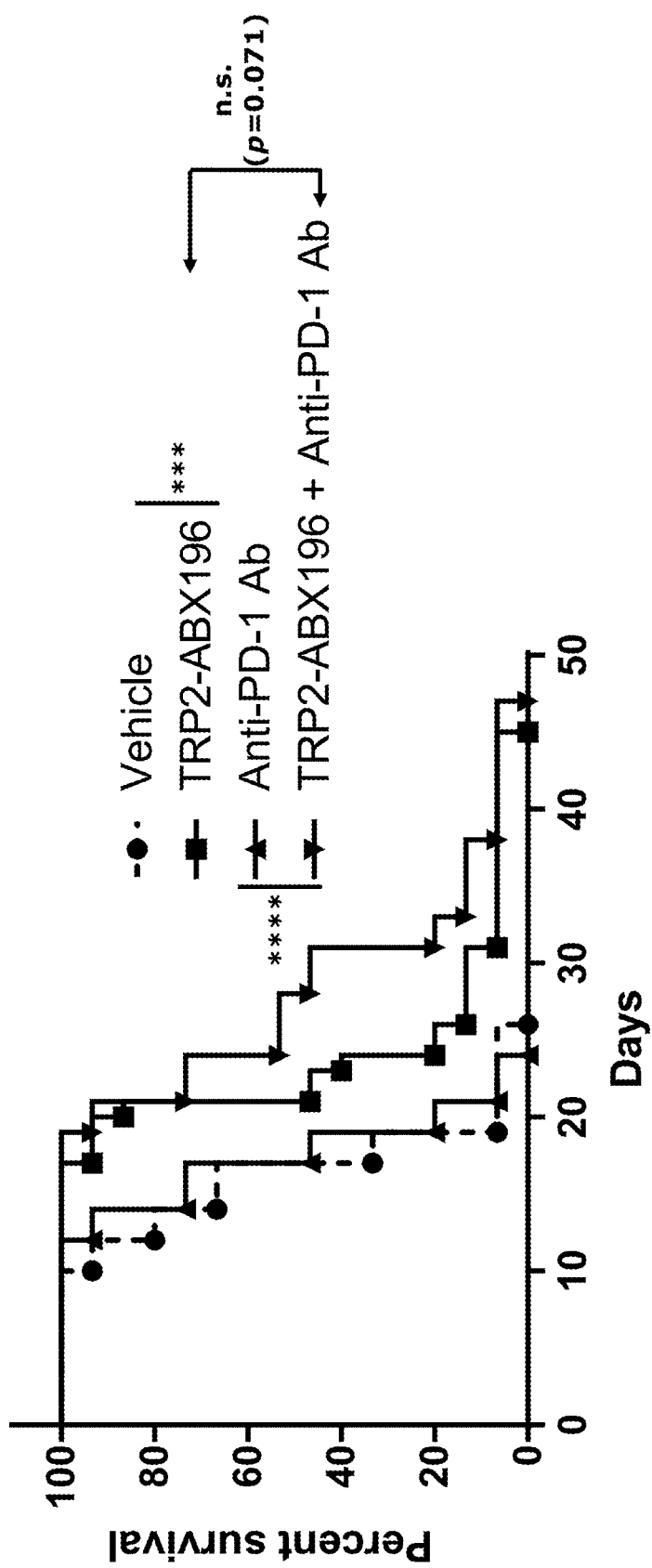
FIG. 2: Survival of C57BL/6 mice bearing B16-F10 tumors and treated, in Example 1, with TRP2-ABX196, anti-PD-1 antibodies or a combination of TRP2-ABX196 and anti-PD-1 antibodies.

Mice survival curves are presented in FIGS. 2 and 4.

A summary of median survival times in days is presented in Table 3 below.

TABLE 3

| Median survival (days) per experimental groups. | |
| --- | --- |
| Treatment group | Median Survival (days) |
| Vehicle | 17 |
| TRP2-ABX196 | 21 |
| Anti-PD-1 Ab | 17 |
| TRP2-ABX196 + Anti-PD-1 Ab | 28 |
| Doxorubicin | 21 |
| TRP2-ABX196 + Doxorubicin | 26 |

The statistical analysis of tumor volume at D17 are shown in Table 4 below.

TABLE 4

Statistical analysis of tumor growth between treatments at D17. Global comparison of all treatments at D17: P value < 0.0001 (Kruskal-Wallis test). Pairwise comparisons between treatments: P value according to the Dunn's multiple comparison test.

| Treatment groups | Vehic. | TRP2-ABX196 | α-PD-1 | TRP2-ABX196 + α-PD-1 | Doxo. | TRP2-ABX196 + Doxo. |
| --- | --- | --- | --- | --- | --- | --- |
| Vehic. | — | ns | ns | *** | ns | *** |
| TRP2-ABX196 | ns | — | ns | ns | ns | ns |
| α-PD-1 | ns | ns | — | *** | ns | **** |
| TRP2-ABX196 + α-PD-1 | *** | ns | *** | — | ns | ns |
| Doxo. | ns | ns | ns | ns | — | * |
| TRP2-ABX196 + Doxo. | *** | ns | **** | ns | * | — |

Vehic.: vehicle;
α-PD-1: anti-PD-1 antibody;
Doxo.: doxorubicin
* P < 0.05;
*** P < 0.001;
**** P < 0.0001

The statistical analysis of tumor volume at D19 are shown in Table 5 below.

TABLE 5

Statistical analysis of tumor growth between treatments at D19. Global comparison of all treatments at D19: P value < 0.0001 (Kruskal-Wallis test). Pairwise comparisons between treatments: P value according to the Dunn's multiple comparison test.

| Treatment Groups | Vehic. | TRP2-ABX196 | α-PD-1 | TRP2-ABX196 + α-PD-1 | Doxo. | TRP2-ABX196 + Doxo. |
| --- | --- | --- | --- | --- | --- | --- |
| Vehic. | — | ns | ns | ns | ns | ** |
| TRP2-ABX196 | ns | — | ns | ns | ns | ns |
| α-PD-1 | ns | ns | — | ** | ns | *** |
| TRP2-ABX196 + α-PD-1 | ns | ns | ** | — | ns | ns |

TABLE 5-continued

Statistical analysis of tumor growth between treatments at D19. Global comparison
of all treatments at D19: P value < 0.0001 (Kruskal-Wallis test). Pairwise comparisons
between treatments: P value according to the Dunn's multiple comparison test.

| Treatment Groups | Vehic. | TRP2-ABX196 | α-PD-1 | TRP2-ABX196 + α-PD-1 | Doxo. | TRP2-ABX196 + Doxo. |
|---|---|---|---|---|---|---|
| Doxo. | ns | ns | ns | ns | — | * |
| TRP2-ABX196 + Doxo. | ** | ns | *** | ns | * | — |

Vehic.: vehicle;
α-PD-1: anti-PD-1 antibody;
Doxo.: doxorubicin
* $P < 0.05$;
** $P < 0.01$;
*** $P < 0.001$;
**** $P < 0.0001$ The statistical analysis of tumor volume at D17 and D19 in three subgroups are shown in Table 6 below.

TABLE 6

Statistical analysis of tumor growth between three
subgroups at D17 and D19.
Statistical analysis of three groups with TRP2-ABX196
as the reference group:

|  | D17 | D19 |
|---|---|---|
| P value - Kruskal-Wallis test[a] | 0.0228 | 0.0121 |
| TRP2-ABX196 + Anti-PD-1 Ab[b] | * | ns |
| TRP2-ABX196 + Doxorubicin[b] | * | ** |

[a]three groups (TRP2-ABX196, TRP2-ABX196 + Anti-PD-1 Ab and TRP2-ABX196 + Doxorubicin are considered)
[b]Dunn's multiple comparison test with TRP2-ABX196 as the reference group
*$P < 0.05$;
**$P < 0.01$;
***$P < 0.001$;
****$P < 0.0001$ The statistical analysis of mice survival are shown in Table 7 below.

TABLE 7

Statistical analysis of mice survival between treatments.
Global comparison of all survival curves: P* < 0.0001
Summary of pairwise comparisons:

| Treatment Groups | TRP2-ABX196 | α-PD-1 | TRP2-ABX196 + α-PD-1 | Doxo. | TRP2-ABX196 + Doxo. |
|---|---|---|---|---|---|
| Vehicle | 0.0001** | 0.279 | <0.0001 | 0.0015 | <0.0001 |
| α-PD-1 | — | | 0.0002 | 0.0710 | 0.624 | 0.22 |
| Doxo. | | | <0.0001 | — | 0.1285 |

α-PD-1: anti-PD-1 antibody;
Doxo.: doxorubicin
*Log-rank (Mantel-Cox) test
**bold numbers refers to significant difference between compared groups ($P < 0.05$).

TABLE 8

Anti-tumor activity index at day 14.

|  | TRP2/ABX196 | Anti-PD-1 | Doxorubicin | TRP2/ABX196 + Anti-PD-1 | TRP2/ABX196 + Doxorubicin |
|---|---|---|---|---|---|
| T/C | 33.5 | 99.8 | 56.3 | 11.8 | 15.4 |
| TGI | 63.1 | 22.5 | 52.7 | 90.5 | 78.5 |

Antitumor Activity Analysis of TRP2-ABX196 Combined with Anti-PD-1 Ab

Mice bearing B16-F10 tumors were treated at D3 with TRP2-ABX196 vaccine, anti-PD-1 Ab at D10, D14, D17 and D21 or a combination of both. The kinetics of tumor growth is shown in FIG. 1.

As expected, there was no anti-tumoral activity associated with anti-PD-1 Ab treatment in comparison to the vehicle-treated group. Those observations are supported by the T/C and TGI values showing that anti-PD-1 demonstrates any activity (Table 8; T/C>42% and TGI<50%). In contrast, mice treatment with TRP2-ABX196 resulted in a slower growth of B16-F10 tumors in comparison to that of the vehicle-treated group. T/C and TGI values reflect the anti tumor activity of TRP2/ABX196 activity (Table 8; T/C<42% and TGI>50%). The antitumor activity of TRP2/ABX196 is further improved in combination with anti-PD-1 antibody, with a complete stabilization of tumor growth up to day 14 in the latter group; as also indicated by T/C and TGI values (Table 8) which are below 15% and higher than 90%, respectively. Those values indicate a highly active treatment because following NCI guidelines, a T/C below 15% demonstrates the high potency of the treatment.

Rigorous and thorough statistical analysis of tumor growth at D17 (Table 5) indicated a significant difference of tumor volume between all groups and a highly significant decrease of tumor volume for the group of mice treated with TRP2-ABX196 vaccine and anti-PD-1 only in comparison to the vehicle-treated group.

With the aim of increasing the power of the statistical analysis and evidenced a difference in the combination group versus the vaccine-treated group, a subsequent statistical analysis was performed with three groups, i.e. TRP2-ABX196, TRP2-ABX196+Anti-PD-1 Ab and TRP2-ABX196+Doxorubicin (Table 6). This analysis indicated a significant decrease of tumor volume at D17 between TRP2-ABX196 and TRP2-ABX196 combined with anti-PD-1 antibody while this difference did not reach significance at day 19.

Mice survival is illustrated in FIG. 2. Survival of mice treated with TRP2-ABX196 and TRP2-ABX196 combined with anti-PD-1 antibody was significantly improved in comparison to that of the vehicle-treated group (Table 7) while the increase was close to significance (P=0.0710) for the combination treatment in comparison to TRP2-ABX196 vaccine alone.

Antitumor Activity Analysis of TRP2-ABX196 Combined with Doxorubicin

Mice bearing B16-F10 tumors were treated at D3 with TRP2-ABX196 vaccine, doxorubicin at D7 or a combination of both. The kinetics of tumor growth is shown in FIG. 3.

Mice treated with doxorubicin alone presented a weak and non-significant (Tables 4 and 5) decrease of tumor growth in comparison to the vehicle-treated group. Even if TGI is slightly higher than 50%, the T/C value remains superior to 42%, indicating the lack of antitumor potency of Doxorubicin. Mice treated with the combination of TRP2-ABX196 in combination with doxorubicin presented a complete stabilization of tumor growth up to day 14; the decrease in tumor volume at D17 and D19 reached significance versus the vehicle-treated group upon the complete statistical analysis of the experiment (Tables 4 and 5). The synergic effect of TRP2/ABX196 and Doxorubicin is also demonstrated by the T/C and TGI values which are <42% and >50%, respectively (Table 8).

Following a subsequent statistical analysis with three groups (Table 6), a significant decrease of tumor volume at D17 and D19 between TRP2-ABX196 and TRP2-ABX196 combined with doxorubicin was found.

Mice survival is illustrated in FIG. 4. Survival of mice treated with TRP2-ABX196 combined with doxorubicin was significantly improved in comparison to that of the vehicle-treated group (Table 7) while the survival increase did not reach significance in comparison to each treatment modality alone.

A synthesis of the median survival for all the experimental groups is shown in Table 3.

5. Conclusions

The purpose of this example was to combine the TRP2-ABX196 vaccine with either an anti-PD-1 antibody or the chemotherapeutic agent doxorubicin, known to induce immunogenic cell death.

The compounds tested, either alone or in combination were well tolerated by the animals and no drug-related severe toxicity nor death were recorded.

Transient weight loss close to 10% was observed in all the groups that received TRP2-ABX196 vaccine but all the mice recovered their normal weight rapidly, i.e. 2 to 5 days after the single vaccine injection.

The survival of mice treated with TRP2-ABX196 vaccine was significantly improved in comparison to the vehicle-treated group. For both combination groups, the anti-tumoral activity was further improved when compared to the vaccine alone with a median survival of 21 days that increased to 28 and 26 days, when combined with anti-PD-1 antibody or doxorubicin, respectively. Survival increase was close to significance with the combination of TRP2-ABX196 vaccine and anti-PD-1 antibody (P=0.071) versus vaccine alone. Even if TRP2/ABX196 and Doxorubicin treatments present an anti-tumor effect, those treatments are improved by the combination of the invention (ABX196 plus anti-PD-1 or plus Doxorubicin) as reflected by T/C ratio, which is lower than 16% when mice are treated with the combinations (see Table 8). Below 15%, treatment is considered as highly active following NCI guidelines. On the same line, the TGI (tumor growth inhibition) is up to 78% in presence of combination treatments, demonstrating that the combination treatment is highly active.

These results are remarkable in the context of the strong agressivity of the B16-F10 model and its poor noteworthy immunogenicity. Of note, the experiment has been performed with a high number of injected tumor cells, i.e. one million per animal, which might potentially explain why complete regressions of tumors were not observed.

Example 2

This example describes the specific effect obtained with the vaccine composition of the invention comprising ABX196 as adjuvant, compared to other vaccine compositions comprising other α-galactosylceramide derivatives as adjuvant.

Materials and Methods

The experiment was performed as described in Example 1 except that mice were administered with $5 \times 10^5$ B16-F10 cells.

The other α-galactosylceramide derivative used was α-GalCer of the following formula:

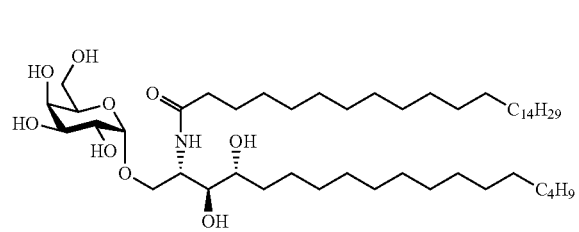

The treatment schedule of the first experiment was as follows:

| Group | No Animals | Treatment | Dose | Route | Treatment schedule |
|---|---|---|---|---|---|
| 1 | 15 | Vehicle | — | IV | Q1Dx1 on D7/D10 |
| 2 | 15 | ABX196 | 100 ng | IV | Q1Dx1 on D10 |
| 3 | 15 | α-GalCer | 100 ng | IV | Q1Dx1 on D10 |
| 4 | 15 | Doxorobucin | 12 mg/kg | IV | Q1Dx1 on D7 |
| 5 | 15 | Doxorobucin | 12 mg/kg | IV | Q1Dx1 on D7 |
|   |    | ABX196 | 100 ng | IV | Q1Dx1 on D10 |
| 6 | 15 | Doxorobucin | 12 mg/kg | IV | Q1Dx1 on D7 |
|   |    | α-GalCer | 100 ng | IV | Q1Dx1 on D10 |
| TOTAL | 90 | | | | |

The treatment schedule of the second experiment was as follows:

| Group | No Animals | Treatment | Dose | Route | Treatment schedule |
|---|---|---|---|---|---|
| 1 | 15 | Vehicle | — | IV | Q1Dx1 on D7/D10 |
| 2 | 15 | ABX196 | 10 ng | IV | Q1Dx1 on D10 |
| 3 | 15 | α-GalCer | 10 ng | IV | Q1Dx1 on D10 |
| 4 | 15 | ABX196 | 100 ng | IV | Q1Dx1 on D10 |
| 5 | 15 | α-GalCer | 100 ng | IV | Q1Dx1 on D10 |
| 6 | 15 | Doxorobucin | 12 mg/kg | IV | Q1Dx1 on D7 |
| 7 | 15 | Doxorobucin | 12 mg/kg | IV | Q1Dx1 on D7 |
|   |    | ABX196 | 10 ng | IV | Q1Dx1 on D10 |
| 8 | 15 | Doxorobucin | 12 mg/kg | IV | Q1Dx1 on D7 |
|   |    | ABX196 | 100 ng | IV | Q1Dx1 on D10 |
| 9 | 15 | Doxorobucin | 12 mg/kg | IV | Q1Dx1 on D7 |
|   |    | α-GalCer | 10 ng | IV | Q1Dx1 on D10 |
| 10 | 15 | Doxorobucin | 12 mg/kg | IV | Q1Dx1 on D7 |
|   |    | α-GalCer | 100 ng | IV | Q1Dx1 on D10 |
| TOTAL | 150 | | | | |

The treatment schedule of the third experiment was as follows:

| Group | No Animals | Treatment | Dose | Route | Treatment schedule |
|---|---|---|---|---|---|
| 1 | 15 | Vehicle | — | IV/IP | D3-IV/TWx2 IP |
| 2 | 15 | TRP2/ABX196 | 50 µg/1 µg | IV | Q1Dx1 on D3 |
| 3 | 15 | Anti-PD-1 Ab | 10 mg/kg | IP | TWx2 on D10/D14/D17/D21 |
| 4 | 15 | TRP2/ABX196 Anti-PD-1 Ab | 50 µg/1 µg 10 mg/kg | IV IP | Q1Dx1 on D3 TWx2 on D10/D14/D17/D21 |
| 5 | 15 | TRP2/αGalCer | 50 µg/1 µg | IV | Q1Dx1 on D3 |
| 6 | 15 | TRP2/αGalCer Anti-PD-1 Ab | 50 µg/1 µg 10 mg/kg | IV IP | Q1Dx1 on D3 TWx2 on D10/D14/D17/D21 |
| TOTAL | 90 | | | | |

The treatment schedule of the fourth experiment was as follows:

| Group | No. Animals | Treatment | Dose | Route | Treatment Schedule |
|---|---|---|---|---|---|
| 1 | 10 | Vehicle | — | IV/IP | D3-IV/TWx2 IP |
| 2 | 10 | TRP2/ABX196 | 50 µg/1 µg | IV | Q1Dx1 on D3 |
| 3 | 10 | TRP2/ABX196 Anti-PD-1 Ab | 50 µg/1 µg 10 mg/kg | IV IP | Q1Dx1 on D3 TWx2 on D10/D14/D17/D21 |

5 mice per group were sacrificed and autopsied at D12 and D16.

Tumor was collected and flow cytometry analysis of the following populations was performed:
T Cytotoxic populations: $CD45^+/CD3^+/CD8^+/TNF\alpha$/Perforin/Granzyme
Treg populations: $CD45^+/CD3^+/CD4^+/CD8^-/FoxP3^+$

Example 3

1. Study Aims

Evaluate the anti-tumoral activity of ABX196 and α-Gal-Cer as defined in example 2 in the ectopic B16-F10 melanoma model.
Evaluate the anti-tumoral activity of ABX196 and α-Gal-Cer combined with doxorubicin treatment in the ectopic B16-F10 melanoma model.

2. Materials and Methods

The experiment is the same as for example 1, except for the following.
Test and Reference Substances Vehicles
Doxorubicin was diluted in NaCl 0.9%
ABX196 was provided as a solution at 250 µg/mL
α-Gal-Cer was provided as a solution at 1 mg/mL
Dilution of ABX196 or αGalCer was performed in PBS buffer
The vehicle solution used in group 1 at day 7 contained DMSO diluted in phosphate buffered saline (PBS) at the same final concentration as the ABX196 test item.

Treatment Doses
The ABX196 and α-Gal-Cer compounds were administered at the dose of 10 or 100 ng per mouse.
Doxorubicin was administered at the dose of 12 mg/kg.
Routes of Administration
Test substance was injected by the intra-venous route in the caudal vein of mice (IV, bolus). Doxorubicin was injected intravenously in the caudal vein of mice (IV, bolus)
In all groups, test substances (ABX196 and α-Gal-Cer) were administered at a dose volume of 5 mL/kg/adm (i.e. for one mouse weighing 20 g, 100 µL of test substance was administered) according to the most recent body weight of mice. Doxorubicin was administered at a dose volume of 10 mL/kg/adm.

3. Experimental Design and Treatments 3.1.1. Induction of B16-F10 Tumors in Animals
Tumor was induced by subcutaneous injection of $5 \times 10^5$ B16-F10 cells in 200 µL of PBS buffer into the right flank of one hundred and ninety-five (195) C57BL/6 female animals. The day of tumor cell injection in the right flank was considered as D0.
3.1.2. Treatment Schedule
On D7, one hundred fifty animals (150) out of one hundred and ninety-five (195) were then randomized according to their tumor volume into 10 groups each of 15 animals (groups 1-10). Should the volume at D7 be too small, in particular with mice presenting no measurable tumors, randomization was performed according to their body weight.
A statistical test (analysis of variance) was performed to test for homogeneity between groups using the Vivo Manager® software (Biosystemes, Couternon, France).
The treatment schedule is summarized in the table below:

| Group | No. Animals | Treatment | Dose | Route | Treatment Schedule |
|---|---|---|---|---|---|
| 1 | 15 | Vehicle | — | IV | Q1Dx1 on D7/D10 |
| 2 | 15 | ABX196 | 10 ng | IV | Q1Dx1 on D10 |
| 3 | 15 | a-Gal-Cer | 10 ng | IV | Q1Dx1 on D10 |
| 4 | 15 | ABX196 | 100 ng | IV | Q1Dx1 on D10 |
| 5 | 15 | a-Gal-Cer | 100 ng | IV | Q1Dx1 on D10 |
| 6 | 15 | Doxorubicin | 12 mg/kg | IV | Q1Dx1 on D7 |
| 7 | 15 | Doxorubicin ABX196 | 12 mg/kg 10 ng | IV IV | Q1Dx1 on D7 Q1Dx1 on D10 |
| 8 | 15 | Doxorubicin ABX196 | 12 mg/kg 100 ng | IV IV | Q1Dx1 on D7 Q1Dx1 on D10 |
| 9 | 15 | Doxorubicin a-Gal-Cer | 12 mg/kg 10 ng | IV IV | Q1Dx1 on D7 Q1Dx1 on D10 |
| 10 | 15 | Doxorubicin a-Gal-Cer | 12 mg/kg 100 ng | IV IV | Q1Dx1 on D7 Q1Dx1 on D10 |

The animals from group 1 received one IV injection of test substance vehicle at day 7 and 10.
The animals from group 2 received one IV injection of 10 ng of ABX196 on day 10.
The animals from group 3 received one IV injection of 10 ng of α-Gal-Cer on day 10.
The animals from group 4 received one IV injection of 100 ng of ABX196 on day 10.
The animals from group 5 received one IV injection of 100 ng of α-Gal-Cer on day 10.
The animals from group 6 received one IV injection of Doxorubicin at 12 mg/kg on day 7.
The animals from group 7 received one IV injection of Doxorubicin at 12 mg/kg on day 7 and one IV injection of 10 ng of ABX196 on day 10.

The animals from group 8 received one IV injection of Doxorubicin at 12 mg/kg on day 7 and one IV injection of 100 ng of ABX196 on day 10.

The animals from group 9 received one IV injection of Doxorubicin at 12 mg/kg on day 7 and one IV injection of 10 ng of α-Gal-Cer on day 10.

The animals from group 10 received one IV injection of Doxorubicin at 12 mg/kg on day 7 and one IV injection of 100 ng of α-Gal-Cer on day 10.

Example 4

1. Study Aims

Part 1: Evaluate the anti-tumoral activity of combinations of the vaccine CL II-TRP2/ABX196 or CL II-TRP2/α-Gal-Cer with an anti-PD-1 antibody in the ectopic B16-F10 melanoma model Part 2: characterization of immune infiltrates in B16-F10 tumors from mice treated with CL II-TRP2/ABX196 vaccine alone or combined with anti-PD-1 antibody treatment.

2. Materials and Methods

Part 1 of the experiment is the same as for example 1, except for the following.

Test and Reference Substances Vehicles

Anti-PD-1 antibody was prepared in phosphate buffered saline (PBS) or other suitable vehicle according to manufacturer's recommendation.

The CI II-TRP2 peptide (5 mg/tube) was resuspended in DMSO at a concentration of 50 mg/mL.

The adjuvant ABX196 was provided as a solution at 250 µg/mL

The adjuvant α-Gal-Cer was provided as a solution at 1 mg/mL

The final formulation of the vaccine containing CI II-TRP2 peptide and ABX196 was prepared in phosphate buffered saline (PBS).

The vehicle solution used in group 1 at day 3 contained DMSO diluted in phosphate buffered saline (PBS) at the same final concentration as for the CL II-TRP2/ABX196 vaccine.

Treatment Doses

The peptide CI II-TRP2 was administered at the dose of 50 µg per mouse together with 100 ng of adjuvants ABX196 or α-Gal-Cer.

The anti-PD-1 antibody was administered at the dose of 10 mg/kg.

Routes of Administration

Test substance was injected by the intra-venous route in the caudal vein of mice (IV, bolus). Anti-PD-1 antibody was injected into the peritoneal cavity of mice (Intraperitoneally, IP)

In all groups, test substances were administered at a dose volume of 5 mL/kg/adm (i.e. for one mouse weighing 20 g, 100 µL of test substance was administered) according to the most recent body weight of mice.

Anti-PD-1 antibody was administered at a dose volume of 10 mL/kg/adm.

3. Experimental Design and Treatments

Part I: Antitumor Activity Study of a Vaccine in Combination with PD-1 Targeting Antibody in Mice Bearing Subcutaneous B16-F10 Melanoma i. Induction of B16-F10 Tumors in Animals Tumor was induced by subcutaneous injection of $5 \times 10^5$ of B16-F10 cells in 200 µL of PBS buffer into the right flank of one hundred and fifty-six (156) C57BL/6 female animals. The day of tumor cell injection in the right flank was considered as D0.

ii. Treatment Schedule

On D3, one hundred and twenty animals (120) out of one hundred and fifty-six (156) were then randomized according to their body weight into 9 groups, six of 15 animals (groups 1-6 of ACT2) and 3 of 10 animals (group 1-3 of ACT3).

A statistical test (analysis of variance) was performed to test for homogeneity between groups using the Vivo Manager® software (Biosystemes, Couternon, France).

The animals from group 1 received one IV injection of test substance vehicle at day 3 and 4 IP administrations of test reference vehicle (Antibody) on day 10, 14, 17 and 21.

The animals from group 2 received one IV injection of 50 µg of CI II-TRP2 together with 100 ng of ABX196 on day 3.

The animals from group 3 received 4 IP administrations of anti-PD-1 antibody on day 10, 14, 17 and 21.

The animals from group 4 received one IV injection of 50 µg of CL II-TRP2 together with 100 ng of ABX196 on day 3 and 4 IP administrations of anti-PD-1 antibody on day 10, 14, 17 and 21.

The animals from group 5 received one IV injection of 50 µg of CI II-TRP2 together with 100 ng of α-Gal-Cer on day 3.

The animals from group 6 received one IV injection of 50 µg of CL II-TRP2 together with 100 ng of α-Gal-Cer on day 3 and 4 IP administrations of anti-PD-1 antibody on day 10, 14, 17 and 21.

The treatment schedule is summarized in the table below:

| Group | No. Animals | Treatment | Dose | Route | Treatment Schedule |
|---|---|---|---|---|---|
| 1 | 15 | Vehicle | — | IV/IP | D3-IV/TWx2 IP |
| 2 | 15 | CL II-TRP2/ABX196 | 50 µg/100 ng | IV | Q1Dx1 on D3 |
| 3 | 15 | Anti-PD-1 Ab | 10 mg/kg | IP | TWx2 on D10/D14/D17/D21 |
| 4 | 15 | CL II-TRP2/ABX196 | 50 µg/100 ng | IV | Q1Dx1 on D3 |
|   |    | Anti-PD-1 Ab | 10 mg/kg | IP | TWx2 on D10/D14/D17/D21 |
| 5 | 15 | CL II-TRP2-α-Gal-Cer | 50 µg/100 ng | IV | Q1Dx1 on D3 |
| 6 | 15 | CL II-TRP2-α-Gal-Cer | 50 µg/100 ng | IV | Q1Dx1 on D3 |
|   |    | Anti-PD-1 Ab | 10 mg/kg | IP | TWx2 on D10/D14/D17/D21 |
| TOTAL | 90 | | | | |

Part II: Characterization of Immune T Cell Infiltrates in B16-F10 Melanoma Tumors from Mice Treated with a Vaccine in Combination with PD-1 Targeting Antibody.

The animals from group 1 received one IV injection of test substance vehicle at day 3 and 4 IP administrations of test reference vehicle (Antibody) on day 10, 14, 17 and 21.

The animals from group 2 received one IV injection of 50 µg of CI II-TRP2 together with 100 ng of ABX196 on day 3.

The animals from group 3 received one IV injection of 50 µg of CL II-TRP2 together with 100 ng of ABX196 on day 3 and 4 IP administrations of anti-PD-1 antibody on day 10, 14, 17 and 21.

The treatment schedule is summarized in the table below:

| Group | No. Animals | Treatment | Dose | Route | Treatment Schedule |
|---|---|---|---|---|---|
| 1 | 10 | Vehicle | — | IV/IP | D3-IV/TWx2 IP |
| 2 | 10 | CL II-TRP2/ABX196 | 50 µg/100 ng | IV | Q1Dx1 on D3 |
| 3 | 10 | CL II-TRP2/ABX196 | 50 µg/100 ng | IV | Q1Dx1 on D3 |
|   |    | Anti-PD-1 Ab | 10 mg/kg | IP | Q1Dx2 on D10/D14 |

Immune T cell infiltrates in the tumor were evaluated on D13 and D17. At the time of termination, tumors from 5 mice of each group were collected. For group 2 and 3, balanced proportion between responding and non-responding mice was collected at each day of collection, i.e. D13 and D17.

After removal from the mice, each tumor was weighted and transferred to tubes with RPMI culture medium. The tumor was mechanically disrupted in small pieces of a few mm size with a scalpel and finally crushed with a 1 mL syringe plunger on a 70 µm sieve (Ref. 352350, FALCON). Cells were next counted after trypan blue staining and one million of cells were centrifuged and resuspended in staining buffer (PBS (ref: 17-516F, Lonza), 0.2% BSA (ref: A7030, Sigma, Saint-Quentin-Fallavier, France), 0.02% $NaN_3$ (ref: S2002, Sigma)).

The antibodies directed against the chosen markers were added to the tumor cell suspension, according to the conditions described by the supplier for each antibody. The markers CD45, CD3, CD4, CD8 were detected on the cell surface. The markers FoxP3, TNFalpha, Perforin, Granzyme were detected intracellularly, after cell permeabilization. Isotype control antibodies was used in each case as negative control. The panel of antibodies used to measure the two following populations are listed in the table below:

Treg cell population: CD45+/CD3+/CD4+/CD8−/FoxP3+
T Cytotoxic populations: CD45+/CD3+/CD8+/TNFa/Perforin/Granzyme

| Specificity | Reference | fluorochrome | Provider | Reference of isotype | Isotype | fluorochrome | Provider |
|---|---|---|---|---|---|---|---|
| FoxP3 | 130-093-014 | PE | Miltenyi Biotec | A07796 | IgG1 | PE | Beckman Coulter |
| CD8a | 553036 | PerCP | BD Biosciences | 553933 | IgG2a | PerCP | BD Biosciences |
| CD3 | 561389 | V450 | BD Biosciences | 560457 | IgG2 | V450 | BD Biosciences |
| CD4 | 130-102-444 | VioGreen | Miltenyi Biotec | 130-102-659 | IgG2b | VioGreen | Miltenyi Biotec |
| CD45 | 557659 | APC-Cy7 | BD Biosciences | 552773 | IgG2b | APC-Cy7 | BD Biosciences |
| TNFalpha | 506308 | APC | biolegend | 400412 | IgG1 | APC | biolegend |
| Perforin | 12-9392-82 | PE | eBioscience | 12-4321 | IgG2a | PE | eBioscience |
| Granzyme | 11-8898-82 | FITC | ebioscience | 553988 | IgG2b | FITC | BD Biosciences |

The mixture of cells and antibodies was incubated for 20 to 30 minutes at room temperature in the dark, washed, and resuspended in 200 µL staining buffer. All samples were stored on ice and protected from light until Flow Cytometry analysis.

The stained cells were analyzed with a CyFlow® space flow cytometer (LSR II, BD Biosciences) equipped with 3 excitation lasers at wavelengths 405, 488 and 633 nm. Flow cytometry data were acquired until either 10,000 mCD45+ events are recorded for each sample, or for a maximum duration of 2 minutes.

Example 5: Study of ABX196 Administered Intravenously or Intratumorally in Combination with Anti-PD-1 Antibodies 1. Study Aims The study was performed on a syngeneic in vivo melanoma B16F10 tumor-bearing mouse model. B16F10 tumor cells were subcutaneously inoculated in immuno-competent C57BL/6 mice.

Melanoma B16F10 tumor cells were subcutaneously inoculated at day 0 by injecting cells in the flank of 8-10 weeks-old female C57BL/6 mice, and animals were then randomly assigned into control (vehicle PBS-treated) and treatments groups.

For the anti-PD-1 antibodies treatment, mice were intraperitoneally (IP) injected with anti-PD-1 antibodies at Day 6, 9, 12, 15 and 21. Furthermore, ABX196 was administered at 1 dose, intravenously or intratumorally, with one administration at Day 10 when mean of tumor size reached 100 $mm^3$.

The animal pharmacological groups for anti-tumor efficacy assessment were organized as such:
Control vehicle-treated group (PBS according to anti-PD-1 treatment schedule)
Anti-PD-1-treated group (at 1 dose, intraperitoneal administration)
ABX196-treated group (at 1 dose, Intravenous (iv) administration at Day 10)
Combination-treated group (ABX196 at 1 dose, Intravenous (iv) administration at Day 10 in combination with anti-PD-1 antibodies at 1 dose, intraperitoneal (ip) administration)
ABX196-treated group (at 1 dose, Intratumoral (it) administration at Day 10)
Combination-treated group (ABX196 at 1 dose, Intratumoral (it) administration at Day 10 in combination with anti-PD-1 antibodies at 1 dose, intraperitoneal (ip) administration)
With:
14-15 mice per group
90 mice in total for the in vivo efficacy assessment 2. Experimental Procedure 2.1 Animals
Mice (*Mus musculus*), Strain C57BL/6, Female
Provider: Charles River Laboratories—BP 0109-F 69592 L'Arbresle Cedex The animals were used between 8 and 10 weeks. 6 weeks-old mice were placed in acclimatization for about 14 days (B16F10 tumor cells implantation at 8 weeks old). 90 animals were used for this study.

Ventilation and air treatment was performed through frequent turnover (8-20 volumes/hour depending on the density of animals housed) and temperature controlled between 22 and 25° C. Humidity was maintained between 40 and 70%. Artificial lighting was maintained 12 hours a day. Quantity and access to food (pellets) and drink (tap water) was checked daily. Mice were housed in collective cages, with 10 animals per cage (820 cm2 cage). Cages were renewed once a week by animal care taker.

2.2 Animal Monitoring

Tumor volume and body weight of the animals were measured and recorded three times per week. A tumor volume exceeding 2000 mm3 or a weight loss greater than 15% relative to the initial weight of the animal were considered as endpoints.

Similarly, if the mouse was (i) prostrate, or (ii) no longer cleaned its coat (hair bristling and not glossy), (iii) was less mobile, this was also considered as an endpoint.

When at least one of these conditions was met then the mice were sacrificed by cervical dislocation.

To minimize pain, suffering and anxiety related to the model, the animals were monitored every 2 days. The observation included reliable criteria such as weight loss (15%) and change of posture. An environmental enrichment was made to minimize anxiety (Plastic tubes).

Pain Procedures:

For operation steps (subcutaneous injection of tumor cells), anesthesia was achieved using Ketamine (0.33 mg/ml) and Xylazine (33.6 µg/ml) by intraperitoneal injection.

2.3 Melanoma Cancer Cells Implantation Procedure
Cancer Cell Line:

Melanoma B16F10 cells were cultured in vitro according to provider's specifications, RPMI 1640 supplemented with FBS at the final concentration of 10%. Before implantation in mice, cell viability was assessed using Trypan Blue exclusion and a cell suspension was prepared according to the viable cell count.

Induction of Melanoma B16F10 Tumors in Mice:

B16F10 cells were implanted subcutaneously in the right flank of C57BL/6 immunocompetent mice (8 week-old female). The implantation procedure was as follows (all steps were carried out under sterile laminar flow conditions): Mice (body weight around 20 g) were anesthetized with an intraperitoneal injection of 90 µL of anesthetic (ie 1.5 mg/Kg Ketamine and Xylazine 150 µg/Kg). The cells to be implanted were resuspended in sterile PBS and the volume needed to implant was loaded in 1 ml syringe with a 25 G needle (1 000,000 cells/100 µL).

2.4 Pharmacological Treatments
Anti-PD-1 Antibodies Treatment
Anti-PD-1 monoclonal antibodies (a-PD-1) treatment schedule was applied, at 100 µg by i.p. injection. Treatment was repeated 4 times, at Days 6, 9, 12, 15 and 18.
27 G gauge needle was used for i.p. injections.
Materials:
Anti-PD-L1 monoclonal antibody (a-PD-1)—(clone RMP1-14)
Anti-PD-1 monoclonal antibody preparation for i.p administration
Anti-PD-1 mAb dissolved in phosphate buffered saline (PBS) solution.
Dulbecco's PBS was used to dissolve anti-PD-1 Ab at a concentration of 1.0 mg/mL (volume of 100 uL). The stock solution was then aliquoted (amount for 1 day treatment) and stored at −20° C.

ABX196 treatment
ABX196 was administered at Day 10 either:
- by intraveneous (i.v) injection at the dose of 100 ng per mouse; or
- by intratumoral (i.t) injection at the dose of 10 ng per mouse Materials:
ABX196 for i.v administration
ABX196 was provided as a solution at 250 µg/mL in PBS. An ABX196 solution at 1 µg/mL was prepared and stored at 4° C. At Day 10, 100 µL of the 1 µg/mL ABX196 solution was injected in the tail vein of the mice from Groups 3 & 4.

ABX196 for i.t administration
ABX196 was provided as a solution at 250 µg/mL in PBS. An ABX196 solution at 0.4 µg/mL was prepared and stored at 4° C. At Day 10, animals from Groups 5 & 6 was anesthetized and 25 µL of the 0.4 µg/mL ABX196 solution were injected in the tumor.

Summary of Pharmacological Treatments

| Group | Tumor cell line | Treatment | n | Host | Dose | Schedule | Route |
|---|---|---|---|---|---|---|---|
| 1 | B16F10 | Vehicle | 20 | C57BL/6 | PBS | Days 6, 9, 12, 15 and 18 | i.p |
| 2 | B16F10 | Anti-PD-1 mAb | 20 | C57BL/6 | 100 µg | Days 6, 9, 12, 15 and 18 | i.p |
| 3 | B16F10 | ABX196 | 20 | C57BL/6 | 100 ng | Day 10 | i.v |
| 4 | B16F10 | Anti-PD-1 mAb + ABX196 | 20 | C57BL/6 | 100 µg Anti-PD-1 mAb 100 ng ABX196 | Days 6, 9, 12, 15 and 18 Day 10 | i.p i.v |
| 5 | B16F10 | ABX196 | 20 | C57BL/6 | 10 ng | Day 10 | i.t |
| 6 | B16F10 | Anti-PD-1 mAb + ABX196 | 20 | C57BL/6 | 100 µg Anti-PD-1 mAb 10 ng ABX196 | Days 6, 9, 12, 15 and 18 Day 10 | i.p i.t |

3. Results

Starting from day 6 after B16F10 cell inoculation, all experimental animal groups were monitored 3 times per week over a 4 weeks period for the following parameters:
- Tumor size: measured by physical examination, 3 times per week,
- Body weight: monitored 3 times per week, and
- Survival: represented in a Kaplan-Meier plot. 3 times per week.

Anti-tumor activity index calculation was the same as for example 1 for the T/C (%) index and the TGI (%).

1. Anti-Tumor Response Assessment a) Tumor Volume

The results are given in FIGS. 5 and 6 showing the mean tumor volume (mm$^3$) of B16F10 bearing mice exposed to the different treatments, post tumor challenge.

In particular, the results show that the combination of Anti-PD-1 Ab with ABX196 according to the invention is more effective in decreasing the tumor volume than ABX196 alone or Anti-PD-1 Ab alone, administered either i.v. or i.t.

The results are also shown in the Tables below.

Statistical analysis of mean tumor volume at Day 17 between the 6 tested groups.

Unpaired t test two tailed, with Welch's correction

| Mean Tumor Volume at Day 17 (p value) | αPD-1 | ABX196 i.v | αPD-1 + ABX196 i.v | ABX196 i.t | αPD-1 + ABX196 i.t |
|---|---|---|---|---|---|
| Vehicle | 0.4473 | 0.2838 | 0.0183 | 0.8942 | 0.0255 |
| αPD-1 | | 0.7081 | 0.012 | 0.2031 | 0.0245 |
| ABX196 i.v | | | 0.0054 | 0.0554 | 0.0169 |
| αPD-1 + ABX196 i.v | | | | <0.0001 | 0.6891 |
| ABX196 i.t | | | | | 0.0001 |
| αPD-1 + ABX196 i.t | | | | | |

| Mean Tumor Volume at Day 17 (Significativity) | αPD-1 | ABX196 i.v | αPD-1 + ABX196 i.v | ABX196 i.t | αPD-1 + ABX196 i.t |
|---|---|---|---|---|---|
| Vehicle | NS | NS | * | NS | * |
| αPD-1 | | NS | * | NS | * |
| ABX196 i.v | | | ** | NS | * |
| αPD-1 + ABX196 i.v | | | | **** | NS |
| ABX196 i.t | | | | | *** |
| αPD-1 + ABX196 i.t | | | | | |

Vehicle is the reference groups.
Mean +/− SEM.
Log-rank (Mantel-Cox) test was performed using Graph Pad Prism→ Mean +/− SEM.
Log-rank (Mantel-Cox) test was performSignificative;
* $p < 0.05$;
** $p < 0.01$;
*** $p < 0.001$;
** $p < 0.0001$ b) Survival The results are given in FIGS. 7 and 8** showing the survival of B16F10 bearing mice exposed to the different treatments, post tumor challenge.

In particular, the results show that the combination of Anti-PD-1 Ab with ABX196 according to the invention lead to a higher percentage of survival than ABX196 alone or than Anti-PD-1 Ab alone, administered either i.v. or i.t.

c) Antitumor Activity Index

| | ABX196 iv | Anti-PD-1 | ABX196 it | Anti-PD-1 + ABX196 iv | Anti-PD-1 + ABX196 it |
|---|---|---|---|---|---|
| T/C | 51 | 76 | 53 | 42 | 37 |

Conclusion:

This study aimed at evaluating the benefit of ABX196 combined with PD-1 blockade in a syngeneic mouse model of melanoma.

There was no effect of anti-PD-1 antibody, even a supplemental dose has been administered at Day 18. The lack of effect was observed at both tumor volume (FIGS. 5 and 6) and survival levels (FIGS. 7 and 8).

Also, a transient effect of ABX196 was observed at early time points after its administration (either iv or it), it didn't translated into a significant effect.

However, it was interesting to observe a synergistic effect between ABX196 and the anti-PD1 Ab. Indeed, ABX196 was able to enhance the anti-PD-1 effect—which was not effective at all. This synergistic effect was observable with both iv and it administration of ABX196. In particular, it was observable at tumor volume level (FIGS. 5 and 6) with significative difference between anti-PD-1 and anti-PD-1+ ABX196 (iv or it) (p=0.012 and 0.0245 respectively). Survival data clearly demonstrated a benefit of combinatory ABX196 and the anti-PD-1 Ab vs vehicle.

Example 6: Determination of the Anti-Tumoral Activity of ABX196 Administered Systemically Alone or Combined with Anti-PD-1 Antibody in Colon and Bladder Cancers 1. Materials and Methods 1.1. Test and Reference Substances
1.1.1. Test Substances
ABX196.
1.1.2. Reference Substances
Anti-PD-1 antibody (ref.: BE0146, BioXcell; clone: RMP1-14, reactivity: mouse; isotype: Rat IgG2a; storage conditions: +4° C.).

1.1.3. Test and Reference Substances Vehicles
Anti-PD-1 antibody were prepared in phosphate buffered saline (PBS) or other suitable vehicle according to manufacturer's recommendation.
ABX196 was provided as a solution at 250 μg/mL.
1.2. Treatment Doses
ABX196 was administered at the dose of 100 ng per mouse. The anti-PD-1 antibody was administered at the dose of 10 mg/kg.
1.3. Routes of Administration
Test substance was injected by the intravenous route in the caudal vein of mice (IV, bolus).
Anti-PD-1 antibody was injected into the peritoneal cavity of mice (Intraperitoneally, IP) In all groups, ABX196 was administered at a fixed dose volume of 100 μL (i.e. approximately 5 mL/kg/adm. for one mouse weighing 20 g).
Anti-PD-1 antibody was administered at a dose volume of 10 mL/kg/adm.
1.4. Cancer Cell Line and Culture Conditions
1.4.1. Cancer Cell Line
The cell lines that were used are detailed in the table below:

| Cell line | Type | Specie | Origin |
|---|---|---|---|
| CT-26 | Colon adenocarcinoma | mouse | ATCC a |
| MBT-2 | Bladder carcinoma | mouse | ATCC a | a American Type Culture Collection, Manassas, Va., USA
The CT-26 cell line is an N-nitroso-N-methylurethane- (NNMU) induced, undifferentiated colon carcinoma cell line of BALB/C mice.
The murine MBT-2 cell line was derived from a carcinogen-induced bladder tumor in C3H/HeJ mice. The MBT-2 cell line was obtained from Dr Cozzi, Memorial Sloan Kettering Cancer Center (New York, USA).
1.4.2. Cell Culture Conditions
Tumor cells were grown as monolayer at 37° C. in a humidified atmosphere (5% CO2, 95% air). The culture medium was RPMI 1640 containing 2 mM L-glutamine (ref: BE12-702F, Lonza, Verviers, Belgium) supplemented with 10% fetal bovine serum (ref: 3302, Lonza). Tumor cells were adherent to plastic flasks. For experimental use, tumor cells were detached from the culture flask by a 5-minute treatment with trypsin-versene (ref: BE02-007E, Lonza), in Hanks' medium without calcium or magnesium (ref: BE10-543F, Lonza) and neutralized by addition of complete culture medium.

The cells were counted and their viability were assessed by 0.25% trypan blue exclusion assay.

1.5. Animals

Sixty-three (63) healthy female BALB/c mice, 6-7 weeks old, were obtained from CHARLES RIVER (L'Arbresles) for each models syngeneic to this strain of mice (i.e. CT-26) and 68 (sixty-eight) healthy female C3H/HeJ (C3H/HeOuJ) mice, 6-7 weeks old, were obtained from The Jackson Laboratory (Bar Harbor, Me.) for the MBT-2 model.

Animals were maintained in SPF health status according to the FELASA guidelines. Animal housing and experimental procedures were realized according to the French and European Regulations and NRC Guide for the Care and Use of Laboratory Animals. The housing conditions of the animals were the same as in example 1.

2. Experimental Design and Treatments 2.1. Induction of CT-26, and MBT-2 Tumors in Animals Tumors were induced by subcutaneous injection of $1 \times 10^6$ of CT-26 cells in 200 μL of RPMI 1640 into the right flank of 63 female BALB/C mice. MBT-2 tumors were induced by subcutaneous injection of $1 \times 10^6$ cells in 200 μL of RPMI 1640 into the right flank of sixty-eight (68) female animals.

2.2. Treatment Schedule

The treatment started when the tumors reached a mean volume of 80-120 mm$^3$. Forty-eight animals (48) out of sixty-three (63) for CT-26 model or sixty-eight (68) for the MBT-2 model were randomized according to their individual tumor volume into 4 groups each of 12 animals using Vivo Manager® software (Biosystemes, Couternon, France). A statistical test (analysis of variance, ANOVA) was performed to test for homogeneity between groups. The treatment schedule was as follows:

Animals from group 1 received an IV injection of ABX196 vehicle and an IP injection of anti-PD-1 antibody vehicle,
Animals from group 2 received an IV injection of 100 ng of ABX196,
Animals from group 3 received twice weekly administrations of anti-PD-1 antibody,
Animals from group 4 received an IV injection of 100 ng of ABX196 and twice weekly administrations of anti-PD-1 antibody.

The treatment schedule is summarized in the table below:

| Group | No animals | Treatment | Dose (mg/kg/adm) | Adm. Route | Treatment schedule |
|---|---|---|---|---|---|
| 1 | 12 | Vehicle ABX196 | — | IV | |
| | | Vehicle Anti-PD-1 Ab | — | IP | TWx2 |
| 2 | 12 | ABX196 | 100 ng | IV | Q1Dx1 |
| 3 | 12 | Anti-PD-1 Ab | 10 | IP | TWx2 |
| 4 | 12 | ABX196 | 100 ng | IV | Q1Dx1 |
| | | Anti-PD-1 Ab* | 10 | IP | TWx2 |

*IP injection of anti-PD-1 Ab initiated after the first IV administration of ABX196 (Concomittant administration) without any delay.

2.3. Animal Monitoring 2.3.1. Clinical Monitoring

All study data, including animal body weight measurements, tumor volume, clinical and mortality records, and treatment were scheduled and recorded on Vivo Manager® database (Biosystemes, Dijon, France).

The viability and behavior were recorded every day. Body weights were measured twice a week. The length and width of the tumor were measured twice a week with calipers and the volume of the tumor was estimated by the formula:

$$\text{Tumor volume} = \frac{\text{width}^2 \times \text{length}}{2}$$

Anti-tumor activity index calculation was the same as for example 1 for the T/C (%) index and the TGI (%).

2.4. Statistical Tests

All statistical analyses were performed using Vivo Manager® software (Biosystemes, Couternon, France). Statistical analysis of mean body weights, MBWC, mean tumor volumes at randomization, mean tumor volumes V, mean times to reach V and mean tumor doubling times were performed using ANOVA. Pairwise tests were performed using the Bonferroni/Dunn correction in case of significant ANOVA results. The log-Rank (Kaplan-Meier) test was used to compare the survival curves. A p value<0.05 was considered as significant.

2.5. Humane Endpoints

The humane endpoints were the same as for example 1.

2.6. Necropsy

Necropsy (macroscopic examination) was performed on all terminated animals in the study, and, if possible, on all euthanized moribund or found dead animals.

2.7. Anesthesia

Isoflurane gas anesthesia was used for all procedures: tumor inoculation and i.v. injections.

2.8. Analgesia

Non-pharmacological care was provided for all painful procedures.

Additionally, pharmacological care not interfering with studies (topic treatment) could be provided at the recommendation of the attending veterinarian.

2.9. Euthanasia

Euthanasia of animals was performed by gas anesthesia over-dosage (Isoflurane) followed by cervical dislocation or exsanguination.

3. Results 3.1. Antitumor Activity of the Tested Treatments in Mice Bearing Subcutaneous CT-26 Colorectal Cancer The results are given in FIG. 9 showing the mean tumor volume (mm$^3$) of CT-26 bearing mice exposed to the different treatments, post tumor challenge. In particular, the results show that the combination of the Anti-PD-1 Ab with ABX196 according to the invention is more effective in decreasing the tumor volume than ABX196 alone or the Anti-PD-1A b alone.

The antitumor activity indexes are given in the Table below:

| | ABX196 | Anti-PD-1 | ABX196 + Anti-PD-1 |
|---|---|---|---|
| T/C | 51 | 58 | 40 |
| TGI | 72 | 42 | 80 |

3.2. Antitumor Activity of the Tested Treatments in Mice Bearing Subcutaneous MBT-2 Bladder Cancer The results are given in FIG. 10 showing the mean tumor volume (mm$^3$) of MBT-2 bearing mice exposed to the different treatments, post tumor challenge. In particular, the results show that the combination of the Anti-PD-1 Ab with ABX196 according to the invention is more effective in decreasing the tumor volume than ABX196 alone or the Anti-PD-1 Ab alone.

The antitumor activity indexes are given in the Table below:

|     | ABX196 | Anti-PD-1 | ABX196 + Anti-PD-1 |
| --- | --- | --- | --- |
| T/C | 57 | 78 | 36 |
| TGI | 43 | 22 | 64 |

3.3. Survival

Figure 11:
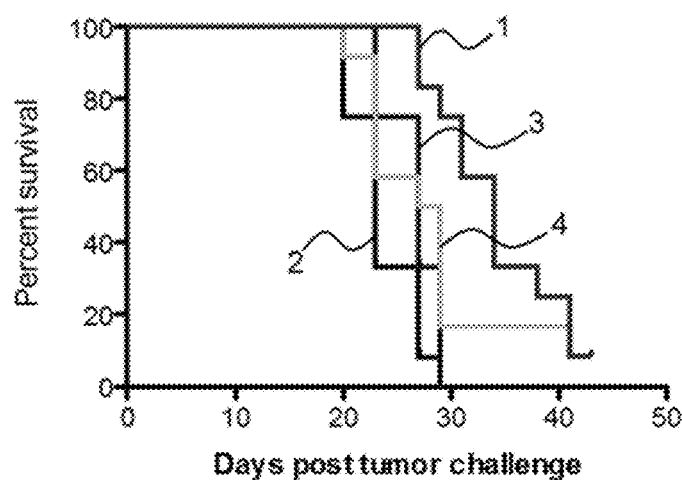

The results are given in FIG. 11 showing the survival of MBT-2 bearing mice exposed to the different treatments, post tumor challenge and in the Table below Median survival (days) per MBT-2 bearing mice from experimental groups.

| Treatment | Median Survival (days) |
| --- | --- |
| Vehicle | 23 |
| ABX196 | 27 |
| Anti-PD-1 | 28 |
| ABX196 + Anti-PD-1 | 34 |

The combination of ABX196 with the Anti-PD-1 antibodies significantly improves the survival of the mice compared to the treatments with ABX196 or Anti-PD-1 antibodies alone.

Statistical analysis of mice survival between treatments.

| Treatment | Vehicle | ABX196 | Anti-PD-1 | ABX196 + Anti-PD-1 |
| --- | --- | --- | --- | --- |
| Vehicle |  | *0.02 | *0.02 | <0.0001**** |
| ABX196 | *0.02 |  | NS | ***0.0002 |
| Anti-PD-1 | *0.02 | NS |  | 0.01* |
| ABX196 + Anti-PD-1 | <0.0001**** | ***0.0002 | 0.01* |  |

Global comparison of all survival curves: p value 0.0045 (***) (Log-Rank (Mantel-cox) test)
Summary of pairwise comparisons 4. Conclusion The tested treatments, either alone or in combination were well tolerated by the animals and no drug-related severe toxicity nor death were recorded.
Antitumor Activity of ABX196 Plus Anti-PD-1 on Colorectal Cancer The tumor growth delay of mice treated with ABX196 plus anti-PD-1 is significantly improved compared to vehicle-treated group (see FIG. 9). The T/C and TGI ratio clearly demonstrate the synergistic effect between ABX196 and anti-PD-1 antibodies. Only the group with ABX196+Anti-PD-1 treatment presents a T/C<42%.
Antitumor Effect on Bladder Cancer Combination of ABX196+anti-PD-1 antibodies reduces significantly the tumor growth (see FIG. 10). The T/C and TGI ratio clearly demonstrate the synergy between ABX196 and anti-PD-1 antibodies. The survival of mice treated with ABX196+anti-PD-1 is significantly improved in comparison to the vehicle-treated group (see FIG. 11). For combination groups, the anti-tumoral activity is further improved when compared to ABX196 alone or anti-PD-1 alone with a median survival of 27 or 28 days that increases to 34 days, when combined with anti-PD-1 antibody.

Example 7: Evaluation of the Anti-Tumoral Activity of ABX196 in Combination with Doxorubicin or Sorafenib or Anti-PD-1 Antibody in the Orthotopic Hepa 1-6 Hepatocarcinoma Model 1. Materials and Methods 1.1 Test and Reference Substances
1.1.1 Test Substances
  ABX196
1.1.2 Reference Substances
  Doxorubicin: DOXO CELL, Cell Pharm.
  Sorafenib (Nexavar®, Bayer Pharma, 200 mg/pill).
  Anti-PD-1 antibody (ref.: BE0146, BioXcell; clone: RMP1-14, reactivity: mouse; isotype:
  Rat IgG2a; storage conditions: +4° C.).
1.2. Test and Reference Substances Vehicles
  Doxorubicin was diluted in NaCl 0.9%
  Anti-PD-1 antibody was prepared in phosphate buffered saline (PBS) or other suitable vehicle according to manufacturer's recommendation.
  Each day of administration to mice, Sorafenib pills were crushed and dissolved first in DMSO (ref: 41640, Fluka, Sigma, Saint Quentin Fallavier, France), then in Tween 20 (ref: P9416, Sigma) followed by NaCl (0.9%) addition (final ratio DMSO/Tween 20/NaCl (0.9%): 5/5/90 v/v) to reach the appropriate concentration of 10 mg/mL.
  The ABX196 was provided as a solution at 250 µg/mL. Dilution of ABX196 was performed in PBS buffer.
  The vehicle solution used in group 1 at day 5 contained DMSO diluted in phosphate buffered saline (PBS) at the same final concentration as the ABX196 test item.
1.3. Treatment Doses
  The ABX196 was administered at the dose of 100 ng per mouse.
  Doxorubicin was administered at the dose of 12 mg/kg.
  The anti-PD-1 antibody was administered at the dose of 10 mg/kg.
  Sorafenib was administered at the dose of 100 mg/kg.
1.4. Routes of Administration
  ABX 196 was injected by the intra-venous route in the caudal vein of mice (IV, bolus). Doxorubicin was administered intravenously in the caudal vein of mice (IV, bolus) Anti-PD-1 antibody was injected into the peritoneal cavity of mice (Intraperitoneally, IP) Sorafenib was administered by oral gavage (per os, PO) via a cannula.
  In all groups, ABX196 was administered at a fixed dose volume of 100 µL (approximately 5 mL/kg/adm for a mouse weighing 20 g). Doxorubicin, anti PD-1 antibody and Sorafenib were administered at a dose volume of 10 mL/kg/adm. according to the most recent body weight of mice.
1.5. Cancer Cell Line and Culture Conditions
1.5.1. Cancer Cell Line
  The cell line that was used is detailed in the table below:

| Cell line | Type | Origin |
| --- | --- | --- |
| Hepa 1-6 | Hepatocellular carcinoma | ATCCa | a: American Type Culture Collection, Manassas, Va., USA
The Hepa 1-6 cell line is a derivative of the BW7756 mouse hepatoma that arose in a C57/L mouse.

1.5.2. Cell Culture Conditions

Tumor cells were grown as monolayer at 37° C. in a humidified atmosphere (5% CO2, 95% air). The culture medium was DMEM containing 4 mM L-glutamine (ref: BE12-604F, Lonza, Verviers, Belgium), 4.5 g/l glucose and 1 mM NaPyr supplemented with 10% fetal bovine serum (ref: 3302, Lonza). The cells were adherent to plastic flasks.

For experimental use, tumor cells were detached from the culture flask by a 5-minute treatment with trypsin-versene (ref: BE17-161E, Lonza), in Hanks' medium without calcium or magnesium (ref: BE10-543F, Lonza) and neutralized by addition of complete culture medium. The cells were counted in a hemocytometer and their viability was assessed by 0.25% trypan blue exclusion assay.

1.5.3. Animals

One hundred (100) healthy female C57BL/6 (C57BLI6J) mice, 5-6 weeks old, were obtained from JANVIER LABS (Le Genest-Saint-Isle).

Animals were maintained in SPF health status according to the FELASA guidelines. Animal housing and experimental procedures were realized according to the French and European Regulations and NRC Guide for the Care and Use of Laboratory Animals. The housing conditions were the same as in example 1.

1.6. Magnetic Resonance Imaging

All imaging experiments were performed on a 4.7 T horizontal magnet (PharmaScan, Bruker Biospin GmbH, Germany) equipped with an actively shielded gradient system. All the MR images were acquired under ParaVision (PV5.1, Bruker Biospin).

1.6.1. Coils and Cradles

Mice were positioned prone in a dedicated mouse body cradle which was slidded in a volume coil (38 mm internal diameter) within the Pharmascan.

1.6.2. Anesthesia and Physiological Monitoring

During all the acquisitions, mice were continuously anesthetized using isoflurane (Minerve, Bondoufle, France) in a mixture of air via a nose piece. The mouse's breathing rate was continuously monitored using a pressure sensor taped on its abdomen. Physiological signals were monitored via a laptop placed next to the MRI workstation and connected to the sensors by fiber optic cables (SA Instruments, USA).

1.6.3. MR Imaging Sequences

Calibration and Positioning

After positioning the animal in the magnet, scout images were acquired for calibration purposes. Sagittal, coronal and axial slices were acquired. At the beginning of this acquisition, automated adjustments were performed to optimize shim, RF power and amplification of the MR signal.

| Type | TE/TR (ms) | Matrix size | FOV (mm) | No of slices | Slice thickness/ spacing (mm) | No averages |
|---|---|---|---|---|---|---|
| FLASH | 6/100 | 128 × 128 | 60 × 60 | NA | 1/NA | 1 |

The sequence used during this step has the following characteristics:
Where: TE is the time to echo, TR is the repetition time, FOV is the field of view.

1.6.4. T2-Weighted (T2w) Anatomical Imaging—Axial Orientation

Anatomical images were acquired using a T2w RARE sequence. The sequence used during this step has the following characteristics:

| Type | TE/TR (ms) | Matrix size | FOV (mm) | No of slices | Slice thickness/ spacing (mm) | No averages |
|---|---|---|---|---|---|---|
| RARE (Rare factor: 8) | 38/2880 | 256 × 192 | 37 × 28 | 15 | 0.8/0.8 | 3 |

If necessary, the FOV size and the sequence parameters were adapted to provide the best imaging results.

1.6.5. Image Processing

All the MR images were transferred to a Windows®-based workstation to be analyzed under ImageJ. Tumor invasion was evaluated semi-quantitavely by a visual evaluation of the percentage of tumor in the entire liver.

2. Experimental Design and Treatments

2.1. Induction of Hepa 1-6 Tumors in Animals by Intrasplenic Injection

One million (1×106) of tumor cells in 50 µL of RPMI 1640 medium were transplanted via intra-splenic injection into 100 C57BL/6 mice. Briefly, a small left subcostal flank incision was made. Spleen was exteriorized. The spleen was exposed on the sterile gauze pad, and injected under visual control with the cell suspension with a 27-gauge needle. After the cell inoculation, the spleen was excised. The day of tumor cell injection was considered as D0.

2.2. Treatment Schedule

The treatment started at D5. Ninety-nine animals (99) out of one hundred (100) were randomized according to their individual body weight into 3 groups of 13 animals and 5 groups of 12 animals using Vivo Manager® software (Biosystemes, Couternon, France). A statistical test (analysis of variance, ANOVA) was performed to test for homogeneity between groups.

The treatment schedule was as follows:
- Animals from group 1 received one IV injection of ABX196 vehicle at day 5,
- Animals from group 2 received one daily PO administration of sorafenib at 100 mg/kg/adm for 21 consecutive days, starting at day 5,
- Animals from group 3 received one IV injection of 100 ng of ABX196 on day 5 and one daily PO administration of sorafenib at 100 mg/kg/adm for 21 consecutive days, starting at day 5,
- Animals from group 4 received one IV injection of Doxorubicin at 12 mg/kg on day 5,
- Animals from group 5 received one IV injection of 100 ng of ABX196 and one IV injection of Doxorubicin at 12 mg/kg on day 5, Animals from group 6 received 4 IP administrations of anti-PD-1 antibody on day 7, 10, 14 and 17 (Twice weekly ×2), Animals from group 7 received one IV injection of 100 ng of ABX196 on day 5 and 4 IP administrations of anti-PD-1 antibody on day 7, 10, 14 and 17 (Twice weekly ×2).

The treatment schedule is summarized in the table below:

| Group | No animals | Treatment | Dose (mg/kg/adm) | Adm. Route | Treatment schedule |
|---|---|---|---|---|---|
| 1 | 13 | Vehicle | NA | IV | Q1Dx1 on D5 |
| 2 | 13 | Sorafenib | 100 | PO | Q1Dx21 start on D5 |
| 3 | 12 | ABX196 | 100 ng | IV | Q1Dx1 on D5 |
|   |    | Sorafenib | 100 | PO | Q1Dx21 start on D5 |
| 4 | 12 | Doxorubicin | 12 | IV | Q1Dx1 on D5 |
| 5 | 12 | ABX196 | 100 ng | IV | Q1Dx1 on D5 |
|   |    | Doxorubicin | 12 | IV | Q1Dx1 on D5 |
| 6 | 12 | Anti-PD-1 | 10 | IP | TWx2 on D7/D10/D14/D17 |
| 7 | 12 | ABX196 | 100 ng | IV | Q1Dx1 on D5 |
|   |    | Anti-PD-1 | 10 | IP | TWx2 on D7/D10/D14/D17 |

2.3. Blood Collection

At D7 and D22, approximately 120 μL of blood were collected by jugular vein puncture into blood collection tubes with clot activator. Tubes were centrifuged 30 minutes after sampling at 1,300 g for 10 minutes at room temperature to obtain serum. The serum samples was stored in propylene tubes at −80° C. All collected serum samples at D22 were analyzed for determination of circulating AFP level by ELISA analysis (Dosage Mouse a-Fetoprotein/AFP, ref: MAFP00, RD Systems).

2.4. MRI Imaging Time Points

At D19 and D20, 5 mice per group from group 1 to 8 were imaged (40 animals per day). A semi-quantitative analysis was then performed.

2.5. Mice Termination

At the time of final mice termination (around D60), liver was weighted. The number of metastases was evaluated macroscopically and the localization, the appearance (shape, colour, consistency) and the size of each of them was recorded. Macroscopic photography of the liver was taken.

Livers/tumors from all animals, sacrificed either for ethical reason or at final termination, were cut into slices 4 mm tick and fixed in 4% neutral buffered formalin for 24 h to 48 h, and then embedded in paraffin (Histosec®, Merck, Darmstadt, Germany).

2.6. Animal Monitoring 2.6.1. Clinical Monitoring

All study data, including animal body weight measurements, clinical and mortality records, and treatment were scheduled and recorded on Vivo Manager® database (Biosystemes, Dijon, France).

The viability and behavior were recorded every day. Body weights were measured thrice a week.

2.6.2. Humane Endpoints
Abdomen diameter superior to 25 mm
Signs of pain, suffering or distress: pain posture, pain face mask, behavior,
Tumors interfering with ambulation or nutrition,
20% body weight loss remaining for 3 consecutive days,
Poor body condition, emaciation, cachexia, dehydration,
Prolonged absence of voluntary responses to external stimuli,
Rapid labored breathing, anemia, significant bleeding,
Neurologic signs: circling, convulsion, paralysis,
Sustained decrease in body temperature,
Abdominal distension.

2.6.3. Necropsy

Necropsy (macroscopic examination) was performed on all terminated animals in the study, and, if possible, on all euthanized moribund or found dead animals.

2.6.4. Surgery

Surgery methods were described in Operating Procedures approved by IACUC.

2.6.5. Anesthesia

Isoflurane gas anesthesia was used for all procedures: surgery and blood collection.

2.6.6. Analgesia

Multimodal carprofen/buprenorphine or xylocaine/buprenorphine analgesia protocol was adapted to the severity of the surgical procedure. Non-pharmacological care was provided for all painful procedures. Additionally, pharmacological care no interfering with studies (topic treatment) could be provided at the recommendation of the attending veterinarian.

2.6.7. Euthanasia

Euthanasia of animals was performed by gas anesthesia over-dosage (Isoflurane) followed by cervical dislocation or exsanguination.

3. Data Presentation 4.1. Health Parameters

The following evaluation criteria of health were determined using Vivo Manager® software (Biosystemes, Couternon, France):

Individual and/or mean (or median) body weights of animals,

Mean body weight change (MBWC): Average weight change of treated animals in percent (weight at day B minus weight at day A divided by weight at day A) was calculated. The intervals over which MBWC was calculated was chosen as a function of body weight curves and the days of body weight measurement.

3.2. Efficacy Parameters

The treatment efficacy was assessed in terms of the effects of the test substance on the tumor volumes of treated animals relative to control animals. The following evaluation criteria of antitumor efficacy were determined:

Individual and/or mean (or median) measurement at D19-20 of tumor invasion within the liver using MRI imaging, Measurement of circulating a-Fetoprotein in the plasma at D22, Liver weight measured at termination, Survival curves,
Median survival times.
Results
Tumor Invasion
The results are given in FIG. 12 showing the percentage of tumor invasion of liver from each treated groups at day 20.

Statistical analysis of tumor invasion between vehicle and each group at day 20. Kruskal-Wallis test p value<0,0001 (****)
Pair wise comparison with Dunn's test

| Dunn's multiple comparisons test | Mean rank diff. | Significant? | Summary |
|---|---|---|---|
| Vehicle vs. Sorafenib | 8.644 | No | ns |
| Vehicle vs. ABX196/Sorafenib | 29.35 | Yes | ** |
| Vehicle vs. Doxorubicin | 28.52 | Yes | ** |
| Vehicle vs. ABX196/Doxorubicin | 27.83 | Yes | * |
| Vehicle vs. Anti-PD-1 | 28.14 | Yes | ** |
| Vehicle vs. ABX196/Anti-PD-1 | 32.77 | Yes | *** |

Summary of alive animals and tumor invasion at day 61.

| Group | Fraction alive | Fraction without detectable metastasis |
|---|---|---|
| 1 Vehicle | 4/13 | 3/13 |
| 2 Sorafenib | 5/13 | 5/13 |
| 3 Sorafenib + ABX196 | 11/12 | 10/12 |
| 4 Doxorubicin | 9/12 | 9/12 |
| 5 Doxorubicin + ABX196 | 8/12 | 6/12 |
| 6 Anti-PD-1 | 11/12 | 10/12 |
| 7 Anti-PD-1 + ABX196 | 12/12 | 12/12 |

CONCLUSION

This experiment demonstrates that combinations including a chemotherapeutic agent or an immunotherapeutic agent and ABX196 are more potent than each component of the combination taken alone.

As shown in FIG. 12, combinations treatments including ABX196 present less tumor invasion. The tumor invasion reduction is transduced into better survival.

The invention claimed is:

1. A method of treating cancer, comprising the administration, in a patient in need thereof, of an antitumor pharmaceutical combination consisting of:

(i) a compound ABX196 of formula (I)

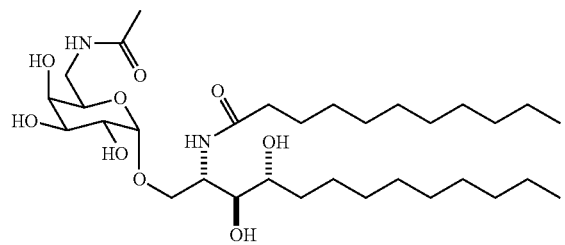

and at least one pharmaceutically acceptable excipient, (ii) a) a therapeutically effective amount of at least one chemotherapeutic agent and at least one pharmaceutically acceptable excipient and/or b) a therapeutically effective amount of at least one immunotherapeutic agent and at least one pharmaceutically acceptable excipient, wherein said at least one immunotherapeutic agent is not an antigen.

2. The method according to claim 1, wherein the compound ABX196 of formula (I) (i)

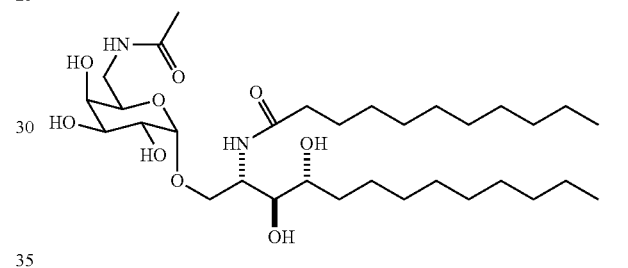

and the at least one chemotherapeutic agent and/or the at least one immunotherapeutic agent (ii) are administered separately.

3. The method according to claim 1, wherein the compound ABX196 of formula (I) (i)

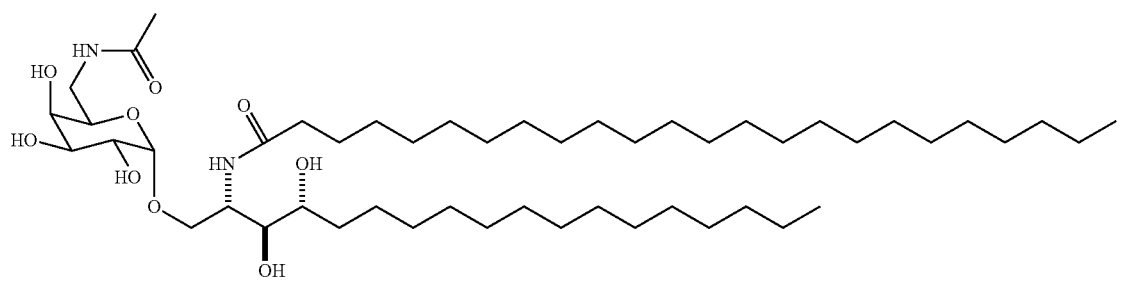

and the at least one chemotherapeutic agent and/or the at least one immunotherapeutic agent (ii) are administered semi-simultaneously.

4. The method according to claim 1, wherein the administrations of the compound ABX196 of formula (I) (i)

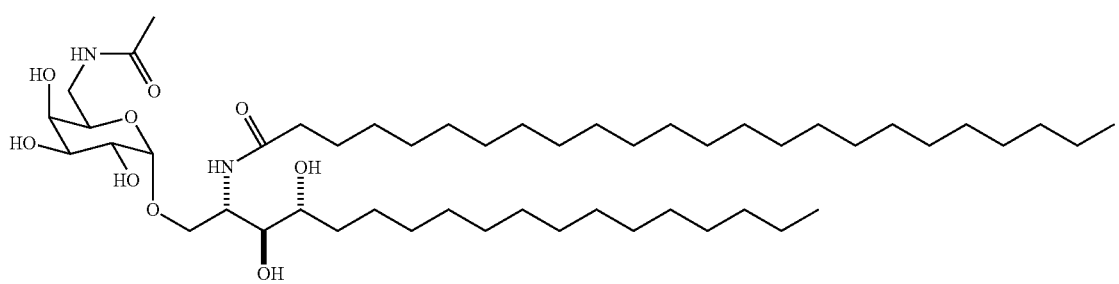
(I)

and of the at least one chemotherapeutic agent and/or the at least one immunotherapeutic agent (ii) are spaced out over a period of time so as to obtain maximum efficacy of the combination.

5. A combined preparation consisting of:
(i) one or more dosage units consisting of a compound ABX196 of formula (I)

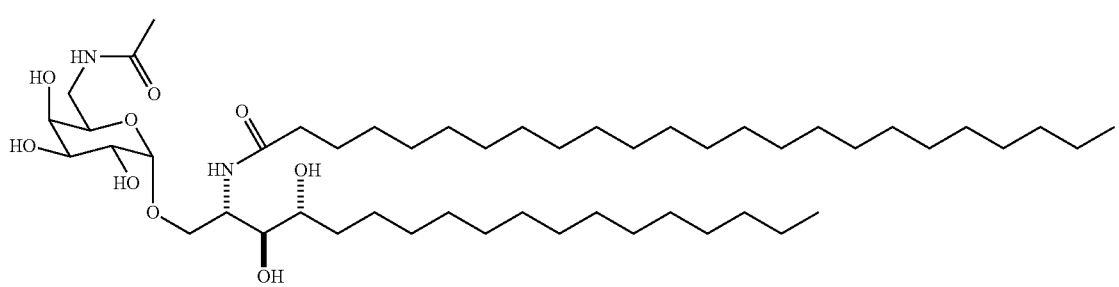
(I)

, and at least one pharmaceutically acceptable excipient, and
(ii) a) one or more dosage units consisting of at least one chemotherapeutic agent and at least one pharmaceutically acceptable excipient and/or b) one or more dosage units consisting of an immunotherapeutic agent and at least one pharmaceutically acceptable excipient,
wherein said at least one immunotherapeutic agent is not an antigen,
for treatment of a cancer.

6. The method according to claim 1, wherein the chemotherapeutic agent is selected from the group consisting of doxorubicin, cyclophosphamide, epirubicin, idarubicin, mitoxantrone and oxaliplatin.

7. The method according to claim 1, wherein the chemotherapeutic agent is doxorubicin or sorafenib.

8. The method according to claim 1, wherein the immunotherapeutic agent is an antibody specific of a tumor antigen selected from the group consisting of Her2/neu, EGFR, VEGF, CD20, CD52, CD33, TACE, cathepsin S, uPA, uPAR, PD-1, Glypican-3, claudin-3, claudin-4, BMCA and CTLA4.

9. The method according to claim 1, wherein the immunotherapeutic agent is a monoclonal anti-PD1 antibody.

10. The method according to claim 1, wherein the cancer is selected from the group consisting of melanoma, hepatocarcinoma, colorectal cancer and bladder cancer.

* * * * *